(12) United States Patent
Yee et al.

(10) Patent No.: US 11,076,879 B2
(45) Date of Patent: Aug. 3, 2021

(54) SHALLOW SURFACE CRYOTHERAPY APPLICATORS AND RELATED TECHNOLOGY

(71) Applicant: Zeltiq Aesthetics, Inc., Pleasanton, CA (US)

(72) Inventors: Peter Yee, San Ramon, CA (US); George Frangineas, Jr., Fremont, CA (US); Austin Root, Pleasanton, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 420 days.

(21) Appl. No.: 15/962,811

(22) Filed: Apr. 25, 2018

(65) Prior Publication Data

US 2018/0310950 A1 Nov. 1, 2018

Related U.S. Application Data

(60) Provisional application No. 62/490,421, filed on Apr. 26, 2017.

(51) Int. Cl.
*A61B 17/30* (2006.01)
*A61F 7/02* (2006.01)
(Continued)

(52) U.S. Cl.
CPC .......... *A61B 17/30* (2013.01); *A61B 18/0218* (2013.01); *A61F 7/02* (2013.01);
(Continued)

(58) Field of Classification Search
CPC ............... A61B 17/30; A61B 18/0218; A61B 2018/0231; A61B 2017/308;
(Continued)

(56) References Cited

U.S. PATENT DOCUMENTS

| 1,681,806 A | 9/1901 | Mignault |
| 2,889,810 A | 6/1908 | Robinson |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

(Continued)

*Primary Examiner* — Linda C Dvorak
*Assistant Examiner* — Nils A Potter
(74) *Attorney, Agent, or Firm* — Perkins Coie LLP

(57) ABSTRACT

Systems for treating a subject's tissue can include a thermally conductive cup with vacuum features configured to facilitate removal of air located between the cup and the subject's skin. The vacuum features can extend along cup to provide airflow paths to a vacuum port. The applicator can cool and/or heat the retained tissue to affect targeted tissue. After the treat period, the vacuum can be reduced or stop and the applicator can be removed from the subject.

23 Claims, 10 Drawing Sheets

(51) Int. Cl.
*A61B 18/02* (2006.01)
*A61B 18/00* (2006.01)
*A61B 17/00* (2006.01)
*A61F 7/00* (2006.01)

(52) U.S. Cl.
CPC ............... *A61B 2017/00561* (2013.01); *A61B 2017/308* (2013.01); *A61B 2018/00041* (2013.01); *A61B 2018/00047* (2013.01); *A61B 2018/00714* (2013.01); *A61B 2018/00791* (2013.01); *A61B 2018/0231* (2013.01); *A61F 2007/0075* (2013.01); *A61F 2007/0093* (2013.01); *A61F 2007/029* (2013.01); *A61F 2007/0239* (2013.01)

(58) Field of Classification Search
CPC ........... A61B 2018/00714; A61B 2018/00047; A61B 2018/00041; A61B 2018/00791; A61B 2017/00561; A61F 7/02; A61F 2007/0239; A61F 2007/0075; A61F 2007/029; A61F 2007/0093
USPC .......................................................... 606/20
See application file for complete search history.

(56) References Cited

U.S. PATENT DOCUMENTS

| | | |
|---|---|---|
| 2,516,491 A | 7/1950 | Swastek |
| 2,521,780 A | 9/1950 | Dodd |
| 2,726,658 A | 12/1955 | Chessey |
| 2,766,619 A | 10/1956 | Myron et al. |
| 2,851,602 A | 9/1958 | Cramwinckel et al. |
| 3,093,135 A | 6/1963 | Hirschhorn |
| 3,132,688 A | 5/1964 | Nowak |
| 3,282,267 A | 11/1966 | William |
| 3,341,230 A | 9/1967 | Louis |
| 3,502,080 A | 3/1970 | Hirschhorn |
| 3,566,871 A | 3/1971 | Richter et al. |
| 3,587,577 A | 6/1971 | Smirnov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van |
| 4,266,043 A | 5/1981 | Fujii et al. |
| 4,269,068 A | 5/1981 | Molina |
| 4,381,009 A | 4/1983 | Del |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdoerffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | Mcdow |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards |
| 5,507,790 A | 4/1996 | Weiss |
| 5,514,105 A | 5/1996 | Goodman et al. |
| 5,514,170 A | 5/1996 | Mauch |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |

(56) References Cited

U.S. PATENT DOCUMENTS

| | | |
|---|---|---|
| 5,700,284 A | 12/1997 | Owens |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein |
| 5,817,149 A | 10/1998 | Owens |
| 5,817,150 A | 10/1998 | Owens |
| 5,830,208 A | 11/1998 | Muller |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | Mcclure et al. |
| 6,049,927 A | 4/2000 | Thomas et al. |
| 6,051,159 A | 4/2000 | Hao |
| 6,071,239 A | 6/2000 | Cribbs et al. |
| 6,074,415 A | 6/2000 | Der |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak et al. |
| 6,494,844 B1 | 12/2002 | Van et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-harcuch et al. |
| 6,551,255 B2 | 4/2003 | Van et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |

(56) References Cited

U.S. PATENT DOCUMENTS

| | | |
|---|---|---|
| 6,795,728 B2 | 9/2004 | Chornenky et al. |
| 6,820,961 B2 | 11/2004 | Johnson |
| 6,821,274 B2 | 11/2004 | Mchale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries et al. |
| 6,942,022 B2 | 9/2005 | Blangetti et al. |
| 6,945,942 B2 | 9/2005 | Van et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,963,959 B2 | 6/2011 | Da et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,247,221 B2 * | 8/2012 | Fawcett ............... B01L 9/523 435/288.4 |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young |
| 8,387,631 B1 * | 3/2013 | Thonghara ............ B08B 5/00 134/104.2 |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | O'connor et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 9,149,323 B2 | 10/2015 | Knowlton |
| 9,581,942 B1 * | 2/2017 | Shippert ............ A61M 1/0056 |
| 2001/0005791 A1 | 6/2001 | Ginsburg et al. |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | Mcintosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Rave et al. |

(56) References Cited

U.S. PATENT DOCUMENTS

| | | |
|---|---|---|
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0035380 A1 | 2/2006 | Saint-leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |
| 2006/0200063 A1 | 9/2006 | Munro et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | Delonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0160480 A1* | 7/2008 | Ruddle ............ A61C 5/40 433/81 |
| 2008/0161892 A1 | 7/2008 | Mercuro et al. |
| 2008/0183164 A1 | 7/2008 | Elkins et al. |
| 2008/0195036 A1* | 8/2008 | Merchant ............ A61N 7/00 604/24 |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Einav et al. |
| 2009/0312693 A1 | 12/2009 | Thapliyal et al. |
| 2009/0326621 A1 | 12/2009 | El-galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da et al. |
| 2010/0152824 A1 | 6/2010 | Allison |
| 2010/0168726 A1 | 7/2010 | Brookman |
| 2010/0198064 A1 | 8/2010 | Perl et al. |
| 2010/0241023 A1 | 9/2010 | Gilbert |
| 2010/0268220 A1* | 10/2010 | Johnson ............ A61B 18/1815 606/33 |
| 2010/0280582 A1* | 11/2010 | Baker ............ A61F 7/007 607/113 |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |

(56) References Cited

U.S. PATENT DOCUMENTS

| | | |
|---|---|---|
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0238050 A1 | 9/2011 | Allison et al. |
| 2011/0238051 A1 | 9/2011 | Levinson et al. |
| 2011/0257642 A1 | 10/2011 | Griggs et al. |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0303904 A1 | 11/2013 | Barthe et al. |
| 2013/0303905 A1 | 11/2013 | Barthe et al. |
| 2014/0005759 A1 | 1/2014 | Fahey et al. |
| 2014/0005760 A1 | 1/2014 | Levinson et al. |
| 2014/0142469 A1 | 5/2014 | Britva et al. |
| 2014/0163582 A1* | 6/2014 | Austen .................. A61B 17/54 606/131 |
| 2014/0200488 A1 | 7/2014 | Seo et al. |
| 2014/0277219 A1 | 9/2014 | Nanda |
| 2015/0216719 A1 | 8/2015 | Debenedictis et al. |
| 2015/0216720 A1 | 8/2015 | Debenedictis et al. |
| 2015/0216816 A1 | 8/2015 | Oneil et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0125424 A1 | 5/2019 | DeBenedictis et al. |
| 2019/0142493 A1 | 5/2019 | DeBenedictis et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 A | 5/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 3065657 U | 4/1999 |
| JP | 2000503154 A | 3/2000 |
| JP | 2001046416 A | 2/2001 |
| JP | 2002125993 A | 5/2002 |
| JP | 2002224051 A | 8/2002 |
| JP | 2002282295 A | 10/2002 |

(56) References Cited

FOREIGN PATENT DOCUMENTS

| | | |
|---|---|---|
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 3655820 B2 | 3/2005 |
| JP | 2005065984 A | 3/2005 |
| JP | 2005110755 A | 4/2005 |
| JP | 2005509977 A | 4/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 3/2000 |
| KR | 20040094508 A | 11/2004 |
| KR | 20090000258 U | 1/2009 |
| KR | 20130043299 A | 4/2013 |
| KR | 20140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

(56) References Cited

OTHER PUBLICATIONS

Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.

(56) References Cited

OTHER PUBLICATIONS

Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schmidt, B. A., et al., "Intradermal adipocytes mediate fibroblast recruitment during skin wound healing," (2013) Development (Cambridge), 140 (7), pp. 1517-1527.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.html?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
"ThermaCool Monopolar Capacitive Radiofrequency, The one choice for nonablative tissue tightening and contouring", Thermage, Inc. Tech Brochure, Nov. 30, 2005, 8 pgs.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

SHALLOW SURFACE CRYOTHERAPY APPLICATORS AND RELATED TECHNOLOGY

CROSS-REFERENCE TO RELATED APPLICATION

The present application claims the benefit of the earlier filing date of U.S. Provisional Patent Application No. 62/490,421, filed Apr. 26, 2017, which is incorporated herein by reference in its entirety.

INCORPORATION BY REFERENCE OF APPLICATIONS AND PATENTS

The following commonly assigned U.S. patent applications and U.S. patents are incorporated herein by reference in their entireties:
U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";
U.S. Pat. No. 6,032,675 entitled "FREEZING METHOD FOR CONTROLLED REMOVAL OF FATTY TISSUE BY LIPOSUCTION";
U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";
U.S. Pat. No. 7,854,754 entitled "COOLING DEVICE FOR REMOVING HEAT FROM SUBCUTANEOUS LIPID-RICH CELLS";
U.S. Pat. No. 8,337,539 entitled "COOLING DEVICE FOR REMOVING HEAT FROM SUBCUTANEOUS LIPID-RICH CELLS";
U.S. Patent Publication No. 2008/0077201 entitled "COOLING DEVICES WITH FLEXIBLE SENSORS";
U.S. Pat. No. 9,132,031 entitled "COOLING DEVICE HAVING A PLURALITY OF CONTROLLABLE COOLING ELEMENTS TO PROVIDE A PREDETERMINED COOLING PROFILE";
U.S. Patent Publication No. 2009/0118722, filed Oct. 31, 2007, entitled "METHOD AND APPARATUS FOR COOLING SUBCUTANEOUS LIPID-RICH CELLS OR TISSUE";
U.S. Patent Publication No. 2009/0018624 entitled "LIMITING USE OF DISPOSABLE SYSTEM PATIENT PROTECTION DEVICES";
U.S. Pat. No. 8,523,927 entitled "SYSTEM FOR TREATING LIPID-RICH REGIONS";
U.S. Patent Publication No. 2009/0018625 entitled "MANAGING SYSTEM TEMPERATURE TO REMOVE HEAT FROM LIPID-RICH REGIONS";
U.S. Patent Publication No. 2009/0018627 entitled "SECURE SYSTEM FOR REMOVING HEAT FROM LIPID-RICH REGIONS";
U.S. Patent Publication No. 2009/0018626 entitled "USER INTERFACES FOR A SYSTEM THAT REMOVES HEAT FROM LIPID-RICH REGIONS";
U.S. Pat. No. 6,041,787 entitled "USE OF CRYOPROTECTIVE AGENT COMPOUNDS DURING CRYOSURGERY";
U.S. Pat. No. 8,285,390 entitled "MONITORING THE COOLING OF SUBCUTANEOUS LIPID-RICH CELLS, SUCH AS THE COOLING OF ADIPOSE TISSUE";
U.S. Pat. No. 8,275,442 entitled "TREATMENT PLANNING SYSTEMS AND METHODS FOR BODY CONTOURING APPLICATIONS";
U.S. patent application Ser. No. 12/275,002 entitled "APPARATUS WITH HYDROPHILIC RESERVOIRS FOR COOLING SUBCUTANEOUS LIPID-RICH CELLS";
U.S. patent application Ser. No. 12/275,014 entitled "APPARATUS WITH HYDROPHOBIC FILTERS FOR REMOVING HEAT FROM SUBCUTANEOUS LIPID-RICH CELLS";
U.S. Pat. No. 8,603,073 entitled "SYSTEMS AND METHODS WITH INTERRUPT/RESUME CAPABILITIES FOR COOLING SUBCUTANEOUS LIPID-RICH CELLS";
U.S. Pat. No. 8,192,474 entitled "TISSUE TREATMENT METHODS";
U.S. Pat. No. 8,702,774 entitled "DEVICE, SYSTEM AND METHOD FOR REMOVING HEAT FROM SUBCUTANEOUS LIPID-RICH CELLS";
U.S. Pat. No. 8,676,338 entitled "COMBINED MODALITY TREATMENT SYSTEMS, METHODS AND APPARATUS FOR BODY CONTOURING APPLICATIONS";
U.S. Pat. No. 9,314,368 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";
U.S. Pat. No. 9,844,461 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";
U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";
U.S. Pat. No. 9,545,523 entitled "MULTI-MODALITY TREATMENT SYSTEMS, METHODS AND APPARATUS FOR ALTERING SUBCUTANEOUS LIPID-RICH TISSUE";
U.S. Pat. No. 9,844,460 entitled "TREATMENT SYSTEMS WITH FLUID MIXING SYSTEMS AND FLUID-COOLED APPLICATORS AND METHODS OF USING THE SAME";
U.S. Pat. No. 9,132,031 entitled "COOLING DEVICE HAVING A PLURALITY OF CONTROLLABLE COOLING ELEMENTS TO PROVIDE A PREDETERMINED COOLING PROFILE;"
U.S. Pat. No. 8,285,390 entitled "MONITORING THE COOLING OF SUBCUTANEOUS LIPID-RICH CELLS, SUCH AS THE COOLING OF ADIPOSE TISSUE;" and
U.S. Pat. No. 9,752,856 entitled "TREATMENT SYSTEMS, SMALL VOLUME APPLICATORS, AND METHODS FOR TREATING SUBMENTAL TISSUE."

TECHNICAL FIELD

The present disclosure relates generally to treatment systems and shallow surface applicators. Several embodiments are directed to applicators with shallow cups with airflow features for air removal.

BACKGROUND

Excess body fat, or adipose tissue, may be present at various locations of a subject's body and may detract from personal appearance. Aesthetic improvement of the human body often involves the selective removal of adipose tissue located at the abdomen, thighs, buttocks, knees, submental region, face and arms, as well as other locations. Invasive procedures (e.g., liposuction), however, tend to be associated with relative high costs, long recovery times, and increased risk of complications. Injection of drugs for reducing adipose tissue can cause significant swelling, bruising, pain, numbness, and/or induration.

Conventional non-invasive treatments for reducing adipose tissue often include regular exercise, application of topical agents, use of weight-loss drugs, dieting, or a combination of these treatments. One drawback of these non-invasive treatments is that they may not be effective or even possible under certain circumstances. For example, when a person is physically injured or ill, regular exercise may not be an option. Topical agents and orally administered weight-loss drugs are not an option if, as another example, they cause an undesirable reaction, such as an allergic or negative reaction. Additionally, non-invasive treatments may be ineffective for selectively reducing specific regions of adiposity, such as localized adipose tissue along the hips, abdomen, thighs, or the like.

Conventional non-invasive vacuum cooling devices suck a fold of skin between two spaced apart cooled plates that are generally parallel to one another. The cooling device can cool and thermally damage targeted tissue. Only opposites sides of the skin fold contact the cooled plates, which limits the cooling capabilities of the cooling devices. Additionally, the end of the tissue fold located in a gap between the plates may experience pooling of blood. A vacuum may cause rupturing of blood vessels and lead to bruising of the skin located in the gap. Accordingly, conventional invasive and non-invasive treatments are not suitable for many subjects and cannot effectively target certain regions of tissue.

BRIEF DESCRIPTION OF THE DRAWINGS

In the drawings, identical reference numbers identify similar elements or acts.

DETAILED DESCRIPTION

A. Overview

Figure 1:
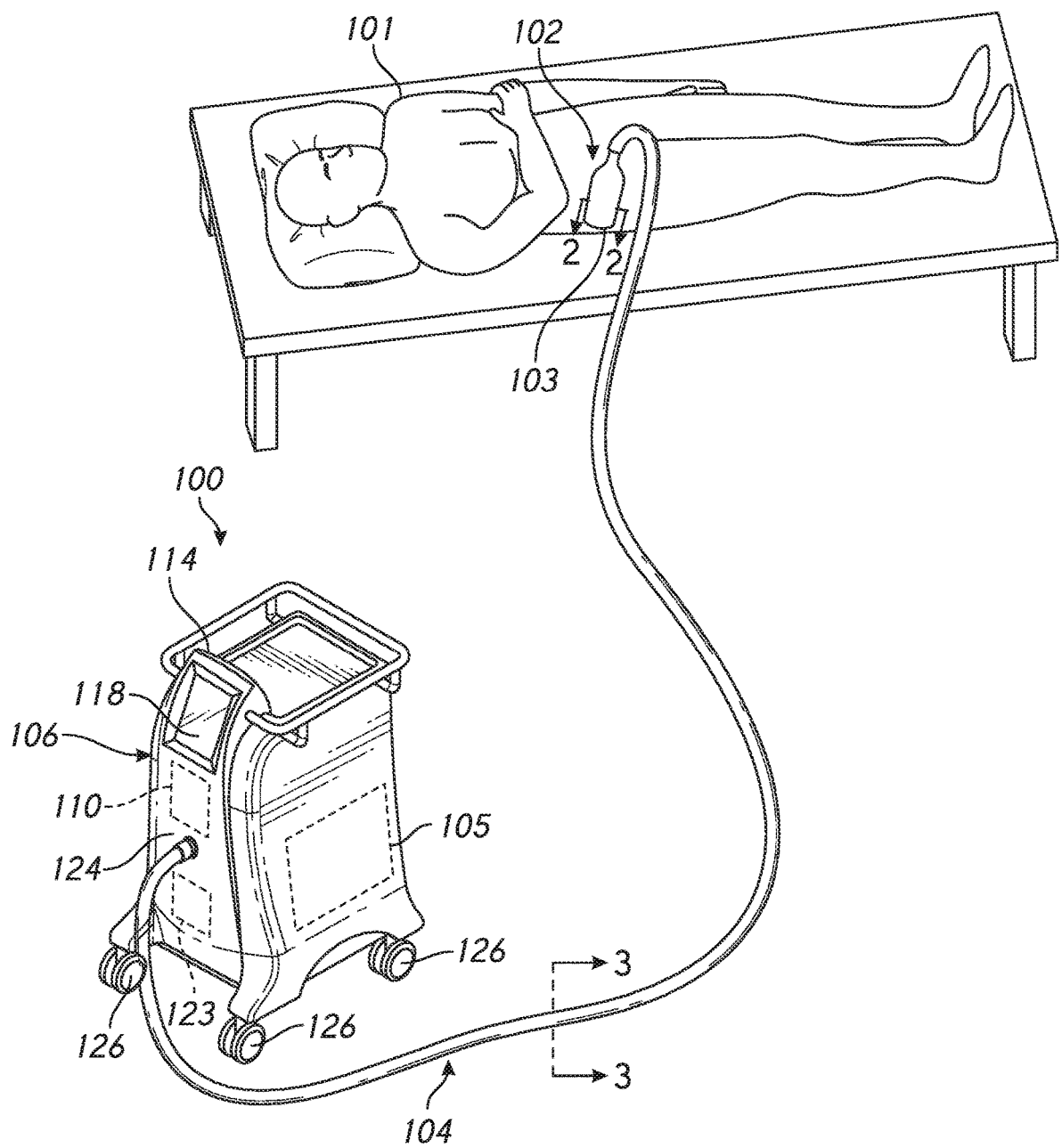
FIG. 1 is a partially schematic, isometric view of a treatment system for non-invasively affecting target regions of a subject in accordance with an embodiment of the technology.

The present disclosure describes treatment systems, applicators, and methods for affecting targeted sites. Several embodiments are directed to non-invasive systems that cool/heat specific regions or volumes of tissue. The non-invasive systems can include applicators with thermally-conductive cooling cups for cooling the skin surface. An applicator can include one or more airflow features that facilitate thermal contact with the tissue. The airflow features can include one or more air-egress features along which air flows to reduce, limit, or substantially eliminate air between the subject's skin and the cup before and/or during treatment. The air-egress features can include small gaps, channels, ridges, protrusions, or other suitable features for defining fluid flow paths. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and methods that are within the scope of the technology but are not described in detail.

Some aspects of the technology are directed to an apparatus that includes an applicator with a temperature-controlled patient contact surface having a topography for providing airflow channels. The airflow channels can extend between a vacuum port and a peripheral portion of the patient contact surface when the patient's tissue is operably received within a cavity of the applicator. The vacuum port can provide communication between the cavity and a pressurization device, such as a vacuum source. The topography of the patient contact surface can be selected to assist in the elimination or reduction of air gaps when the patient's tissue is drawn to the cavity, distribute the vacuum throughout the cavity (e.g., distribute the vacuum along the patient contact surface), and/or otherwise facilitate air removal. In some embodiments, a cup and the vacuum port are configured such that when a vacuum is applied the subject's tissue substantially fills an entire volume of the cup except for small gaps created by air-egress features formed on a surface of the cup.

One aspect the technology is directed to an applicator configured to cool tissue. The applicator can include a cup, at least one vacuum port, and air-egress features. The cup can define a tissue-receiving cavity and can include a temperature-controlled surface. The air-egress features can extend along the temperature-controlled surface to provide airflow paths to the vacuum port to enhance air removal between the subject's skin and the cup while the subject's tissue is pulled toward the temperature-controlled surface. The applicator can draw in air such that the subject's tissue fills most or substantially all of the tissue-receiving cavity. In some embodiments, a vacuum can be drawn to pull the skin into thermal contact with a large area of the cup, thereby providing a relatively large skin/cup interface for heat transfer. For example, the temperature-controlled surface can extend continuously along spaced apart sidewalls and bottom of the cooling cup and can thermally contact an area of the subject's skin that is equal to or less than about 20 cm$^2$, 40 cm$^2$, 80 cm$^2$, 100 cm$^2$, 140 cm$^2$, 160 cm$^2$, 180 cm$^2$, 200 cm$^2$, 300 cm$^2$, or other suitable area. Air can escape via the air-egress features to eliminate air gaps that would impair heat-transfer with the subject's skin. The temperature-controlled conductive surface, including the airflow features, can be cooled to a temperature equal to or lower than a selected temperature (e.g., 5° C., 0° C., −2° C., −5° C., −7° C., −10° C., −15° C., −20° C., −25° C., etc.). In some embodiments, most of the temperature-controlled conductive surface can be cooled to a temperature equal to or lower than about 0° C., −2° C., −5° C., −10° C., or −15° C.

In some embodiments, an apparatus for treating a human subject includes an applicator configured to cool the subject's skin. The applicator includes a cup, at least one vacuum port, and air-egress features. The cup defines a tissue-receiving cavity. The air-egress features can extend along the temperature-controlled surface to provide airflow paths to the vacuum port for removing air located between the subject's skin and the cup while the vacuum port provides a vacuum to draw the subject's tissue toward the temperature-controlled surface. In some embodiments, the air-egress features include channels, ridges, protrusions, or the like.

In certain procedures, one or more liners, cryoprotectant, or other suitable elements can be positioned between the subject's skin and the cup. The liner can have an adhesive surface for adhering to the cup and can be perforated to allow airflow therethrough. The liner assembly can be made, in whole or in part, of plastic, rubber, or other suitable material and can include, without limitation, one or more sealing members, sensors, release liners, carriers, alignment features, or the like. In other procedures, the subject's skin can directly contact the cup.

Some of the embodiments disclosed herein can be for cosmetically beneficial alterations of target regions. Some cosmetic procedures may be for the sole purpose of altering a target region to conform to a cosmetically desirable look, feel, size, shape and/or other desirable cosmetic characteristic or feature. Accordingly, at least some embodiments of the cosmetic procedures can be performed without providing an appreciable therapeutic effect (e.g., no therapeutic effect). For example, some cosmetic procedures may not include restoration of health, physical integrity, or the physical well-being of a subject. The cosmetic methods can target subcutaneous regions to change a human subject's appearance and can include, for example, procedures performed on a subject's submental region, abdomen, hips, legs, face, neck, ankle region, or the like. In other embodiments, however, cosmetically desirable treatments may have therapeutic outcomes (whether intended or not), such as psychological benefits, alteration of body hormone levels (by the reduction of adipose tissue), etc.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

B. Cryotherapy

FIG. 1 and the following discussion provide a brief, general description of a treatment system 100 in accordance with some embodiments of the technology. The treatment system 100 can be a temperature-controlled system for exchanging heat with a subject 101 and can include a non-invasive tissue-cooling apparatus in the form of a cooling cup applicator 102 ("applicator 102") configured to selectively cool tissue to affect targeted tissue, structures, or the like. The illustrated applicator 102 is positioned along a subject's hip and can draw a vacuum to provide suitable thermal contact with the subject's skin to cool subcutaneous adipose tissue. The applicator 102 is configured to facilitate a high amount of thermal contact with the subject's skin by minimizing, limiting, or substantially eliminating air gaps at the applicator/tissue interface. The entire skin surface of the retained volume of tissue can be cooled for efficient treatment. The applicator 102 can have a relatively shallow tissue-receiving chamber to avoid or limit pooling of blood, rupturing of blood vessels, patient discomfort, and so forth.

The applicator 102 can be used to perform medical treatments to provide therapeutic effects and/or cosmetic procedures for cosmetically beneficial effects. Without being bound by theory, selective effects of cooling are believed to result in, for example, membrane disruption, cell shrinkage, disabling, disrupting, damaging, destroying, removing, killing and/or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling can be the selective reduction of lipid-rich cells by a desired mechanism of action, such as apoptosis, lipolysis, or the like. In some procedures, the applicator 102 can cool the skin surface and/or targeted tissue to cooling temperature in a range of from about −25° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures and temperature ranges can be used.

Apoptosis, also referred to as "programmed cell death", is a genetically-induced death mechanism by which cells self-destruct without incurring damage to surrounding tissues.

An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with highly localized adiposity (e.g., adiposity along the abdomen, submental adiposity, submandibular adiposity, facial adiposity, etc.), can be affected while non-lipid-rich cells (e.g., myocytes) in the same generally region are not damaged. The unaffected non-lipid-rich cells can be located underneath lipid-rich cells (e.g., cells deeper than a subcutaneous layer of fat), in the dermis, in the epidermis, and/or at other locations.

In some procedures, the treatment system 100 can remove heat from underlying tissue through the upper layers of tissue and create a thermal gradient with the coldest temperatures near the cooling surface, or surfaces, of the applicator 102 (i.e., the temperature of the upper layer(s) of the skin can be lower than that of the targeted underlying target cells). It may be challenging to reduce the temperature of the targeted cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying cells (e.g., typically water-rich dermal and epidermal skin cells) from freeze damage during dermatological and related aesthetic procedures that involve sustained exposure to cold temperatures may include improving the freeze tolerance and/or freeze avoidance of these skin cells by using, for example, cryoprotectants for inhibiting or preventing such freeze damage.

Tissue can be rapidly rewarmed as soon as practicable after a freeze event has occurred to limit, reduce, or prevent damage and adverse side effects associated with the freeze event. After freezing begins, tissue can be rapidly warmed as soon as possible to minimize or limit damage to tissue, such as the epidermis. In some procedures, tissue is partially or completely frozen for a predetermined period of time and then warmed. According to one embodiment, an applicator can warm shallow tissue using, for example, thermoelectric elements in the device. Thermoelectric elements can include Peltier devices capable of operating to establish a desired temperature (or temperature profile) along the surface. In other embodiments, the applicator outputs energy to warm tissue. For example, the applicator can have electrodes that output radiofrequency energy for warming tissue. In some procedures, the tissue can be warmed at a rate of about 1° C./s, 2° C./s, 2.5° C./s, 3° C./s, 5° C./s, or other rate selected to thaw frozen tissue after the tissue has been partially or completely frozen for about 10 seconds, 30 seconds, 1 minute, 2 minutes, 5 minutes, 10 minutes, or other suitable length of time.

C. Treatment Systems

Figure 2:
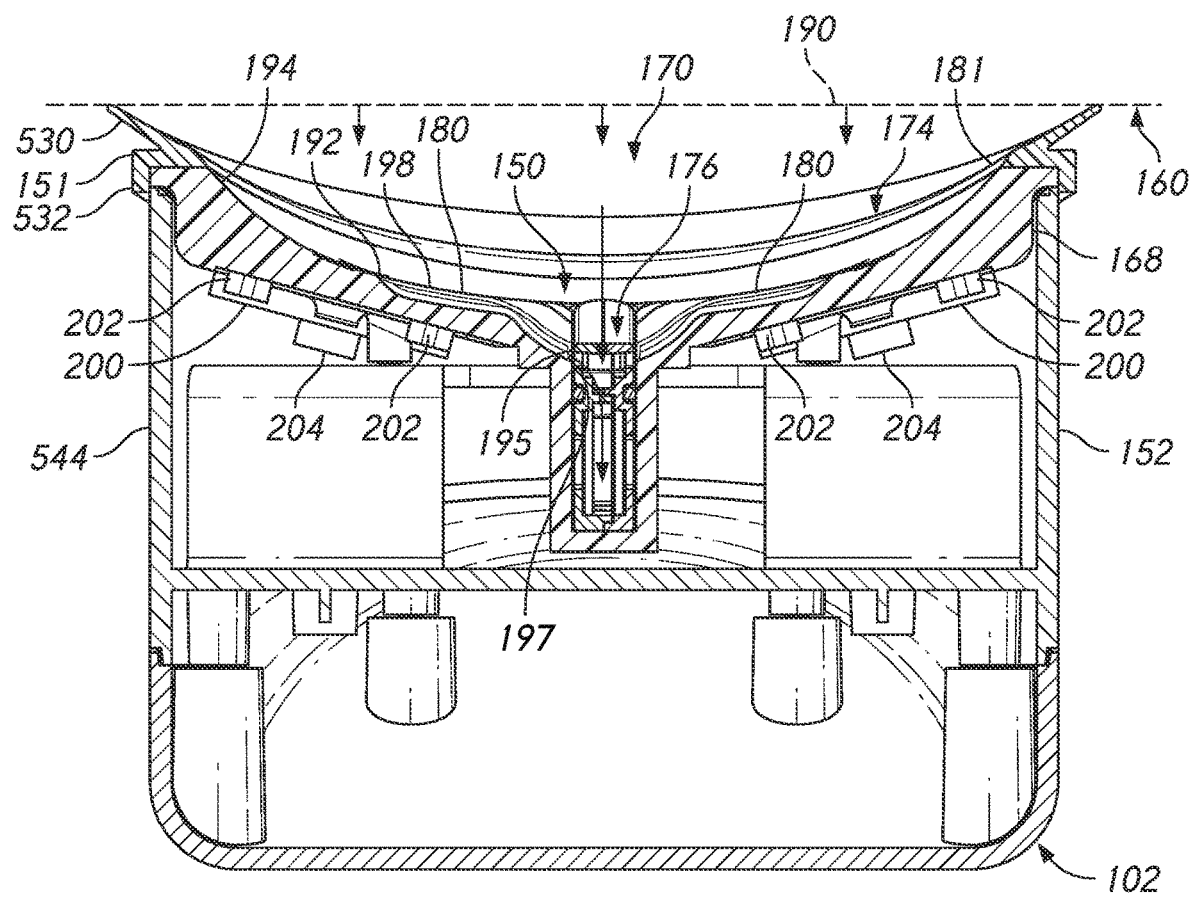
FIG. 2 is a cross-sectional view of an applicator taken along line 2-2 of FIG. 1 and FIG. 5.

FIG. 2 is a cross-sectional view of the applicator 102 taken along line 2-2 of FIG. 1. The applicator 102 includes a contoured sealing element 151 and a base unit 152. The sealing element 151 can conform closely to contours of the subject's body to sealingly engage a liner or skin surface 160. The base unit 152 can include a shallow cup 168 defining a tissue-receiving cavity 170 for holding tissue. The cup 168 can include a temperature-controlled surface 174, a vacuum port 176, and airflow features in the form of air-egress features 180 extending along the bottom of the tissue-receiving cavity 170. Dashed line 190 shows the position of the subject's tissue (or liner) before being drawn (indicated by arrows) into the applicator 102. If a liner is used with the applicator 102, the liner can line the cup 168 and can be perforated such that a vacuum can be drawn through the liner to urge the subject's skin against the liner, thereby maintaining thermal contact between the tissue and the cup 168.

The air-egress features 180 can help distribute the vacuum across the cup/tissue interface to enhance patient comfort and prevent air gaps at the tissue/cup interface during tissue draw. After the subject's tissue fills the tissue-receiving cavity 170, the air-egress features 180 can distribute the vacuum across a large area of the tissue-cup interface. During subcutaneous treatments, the subject's skin can extend across the air-egress features 180, illustrated as channels spreading outwardly from a central region 150 of the cup 168. Constant or varying vacuum levels can be used to keep the tissue in thermal contact with the cup 168. In some embodiments, the vacuum port 176 is positioned at the central region 150 to draw the tissue into the deepest region of the tissue-receiving cavity 170, and the air-egress features 180 extend toward a peripheral portion 181 of the temperature-controlled surface 174. The air-egress features 180 can be a network of elongate protrusions, ridges, and/or channels positioned at locations at which air tends to become trapped. If ambient air is inadvertently sucked between the cup 168 and the subject's skin, it can serve as a thermal insulator and reduce heat transfer between the applicator 102 and the subject's tissue. Such air can be removed via the air-egress features 180 to maintain suitable thermal contact throughout the entire treatment session, including relatively long sessions (e.g., sessions equal to or longer than 20 minutes, 30 minutes, 45 minutes, 1 hour, or 2 hours).

Each air-egress feature 180 can include a first end 192 spaced apart from a mouth 194 of the cup 168, a second end 195 positioned proximate a vacuum port 197, and a main portion 198 extending between the first and second ends 192, 195. Most or substantially all of the skin surface of the volume of tissue in the cavity 170 can be in thermal contact with the cup 168. In some procedures, the vacuum level can be sufficiently high to keep the tissue in contact with the bottom of the cup 168 to keep the cavity 170 filled with tissue but can be sufficiently low to limit or minimize pooling of blood, vascular damage (e.g., rupturing of blood vessels), bruising, and other complications often associated with vacuum-based procedures. Upon completion of the cryotherapy procedure, the applicator 102 can release the tissue (e.g., by reducing or stopping the vacuum) and can be used at another treatment site.

The base unit 152 can include cooling units 200 coupled to, embedded in, or otherwise in thermal communication with the temperature-controlled surface 174. The cooling units 200 can include, without limitation, one or more thermoelectric elements 202 (e.g., Peltier-type elements), fluid-cooled elements 204, heat-exchanging units, or combinations thereof. In a cooling mode, fluid-cooled elements 204 can cool the backside of the thermoelectric elements 202 to keep the thermoelectric elements 202 at or below a target temperature. In a heating mode, fluid-cooled elements 200 can heat the backside of the thermoelectric elements 202 to keep the thermoelectric elements 202 at or above a target temperature. In some embodiments, the cooling units 200 include only fluid-cooled elements or only non-fluid-cooled elements. The cooling units 200 can be embedded or otherwise disposed in the cup 168 to reduce the distance from the tissue to the thermoelectric elements 202. Although the illustrated embodiment has two cooling units 200, it can have any desired number of cooling units 200. The number, positions, configurations, and operating temperatures of the cooling units can be selected based on cooling/heating suitable for treatment, desired power consumption, or the like.

Figure 3:
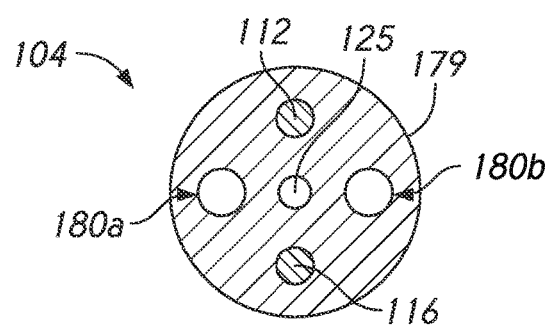
FIG. 3 is a cross-sectional view of a connector taken along line 3-3 of FIG. 1.

Referring again to FIG. 1, the connector 104 extends from the control module 106 to the applicator 102 and can provide suction for drawing tissue into the applicator 102 and energy (e.g., electrical energy) and fluid (e.g., coolant) from the control module 106 to the applicator 102. FIG. 3 is a cross-sectional view of the connector 104 taken along line 3-3 of FIG. 1 and shows the connector 104 including a main body 179, a supply fluid line or lumen 180a ("supply fluid line 180a"), and a return fluid line or lumen 180b ("return fluid line 180b"). Referring now to FIG. 3, the main body 179 may be configured (via one or more adjustable joints) to "set" in place for the treatment of the subject 101. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, a refrigerant, and/or any other suitable heat conducting fluid for passing through fluid-cooled element, such as the fluid-cooled elements (e.g., fluid-cooled elements 204 of FIG. 2), or other components. In one embodiment, each fluid line 180a, 180b can be a flexible hose surrounded by the main body 179.

The connector 104 can also include one or more electrical lines 112 for providing power to the applicator 102 and one or more control lines 116 for providing communication between the control module 106 (FIG. 1) and the applicator 102 (FIGS. 1 and 2). The electrical lines 112 can provide power to the thermoelectric elements, sensors, and so forth. To provide suction, the connector 104 can include one or more vacuum lines 125. In various embodiments, the connector 104 can include a bundle of fluid conduits, a bundle of power lines, wired connections, vacuum lines, and other bundled and/or unbundled components selected to provide ergonomic comfort, minimize unwanted motion (and thus potential inefficient removal of heat from the subject), and/or to provide an aesthetic appearance to the treatment system.

Referring again to FIG. 1, the control module 106 can include a fluid system 105 (illustrated in phantom line), a power supply 110 (illustrated in phantom line), and a controller 114 carried by a housing 124 with wheels 126. The fluid system 105 can include a fluid chamber and a refrigeration unit, a cooling tower, a thermoelectric chiller, heaters, or any other device capable of controlling the temperature of coolant in the fluid chamber. The coolant can be continuously or intermittently delivered to the applicator 102 via the supply fluid line 180a (FIG. 3) and can circulate through the applicator 102 to absorb heat. The coolant, which has absorbed heat, can flow from the applicator 102 back to the control module 106 via the return fluid line 180b (FIG. 3). For warming periods, the control module 106 can heat the coolant that is circulated through the applicator 102.

Alternatively, a municipal water supply (e.g., tap water) can be used in place of or in conjunction with the control module 106.

A pressurization device 123 can provide suction to the applicator 102 via the vacuum line 125 (FIG. 3) and can include one or more vacuum sources (e.g., pumps). Air pockets between the subject's tissue can impair heat transfer with the tissue and, if large enough, can affect treatment. The pressurization device 123 can provide a sufficient vacuum to eliminate such air gaps (e.g., large air gaps between the tissue and the temperature-controlled surface 174 of FIG. 2) such that substantially no air gaps impair non-invasively cooling of the subject's subcutaneous lipid-rich cells to a treatment temperature. When the air pockets are eliminate, the tissue can be suitably cooled even though the air-egress features may contain small volumes of air and may not contact the subject's skin.

Air pressure can be controlled by a regulator located between the pressurization device 123 and the applicator 102. The control module 106 can control the vacuum level to, for example, install the liner assembly and/or draw tissue into the applicator 102 while maintaining a desired level of comfort. If the vacuum level is too low, a liner assembly, tissue, etc. may not be drawn adequately (or at all) into and/or held within the applicator 102. If the vacuum level is too high when preparing the applicator, a liner assembly can break (e.g., rupture, tear, etc.). If the vacuum level is too high during treatment, the patient can experience discomfort, bruising, or other complications. According to certain embodiments, approximately 0.5 inch Hg, 1 inch Hg, 2 inches Hg, 3 inches Hg, 5 inches Hg, 7 inches Hg, 8 inches Hg, 10 inches Hg, or 12 inches Hg vacuum is applied to draw or hold the liner assembly, tissue, etc. In some embodiments, the air-egress features 180 can be configured to maintain the airflow paths when 12 inches Hg vacuum level is used to draw tissue into the tissue-receiving cavity 170. The number, dimensions, and positions of the air-egress features 180 can be selected to achieve desired tissue contact. Other vacuum levels can be selected based on the characteristics of the tissue, desired level of comfort, and vacuum leakage rates. Vacuum leak rates of the applicator 102 can be equal to or less than about 0.2 LPM, 0.5 LPM, 1 LPM, or 2 LPM at the pressure levels disclosed herein. For example, the vacuum leak rate can be equal to or less than about 0.2 LPM at 8 inches Hg, 0.5 LPM at 8 inches Hg, 1 LPM at 8 inches Hg, or 2 LPM at 8 inches Hg. The configuration of the pressurization device 123 and applicator 102 can be selected based on the desired vacuum levels, leakage rates, and other operating parameters.

The power supply 110 can provide a direct current voltage for powering electrical elements of the applicator 102 via the line 112 (FIG. 3). The electrical elements can be thermal devices, sensors, actuators, controllers (e.g., a controller integrated into the applicator 102), or the like. An operator can use an input/output device in the form of a screen 118 ("input/output device 118") of the controller 114 to control operation of the treatment system 100, and the input/output device 118 can display the state of operation of the treatment system 100 and/or progress of a treatment protocol. In some embodiments, the controller 114 can exchange data with the applicator 102 via the line (e.g., link 116 of FIG. 3), a wireless communication link, or an optical communication link and can monitor and adjust treatment based on, without limitation, one or more treatment profiles and/or patient-specific treatment plans, such as those described, for example, in commonly assigned U.S. Pat. No. 8,275,442. The controller 114 can contain instructions to perform the treatment profiles and/or patient-specific treatment plans, which can include one or more segments, and each segment can include temperature profiles, vacuum levels, and/or specified durations (e.g., 1 minute, 5 minutes, 10 minutes, 20 minutes, 30 minutes, 1 hour, 2 hours, etc.). For example, the controller 114 can be programmed to cause the pressurization device to operate to pull tissue into the applicator. After tissue draw, the pressurization device can operate to hold the subject's skin in thermal contact appropriate features while the cup conductively cools tissue. If the sensor detects tissue moving out of thermal contact with the cup, the vacuum can be increased to reestablish suitable thermal contact. In some embodiments, the controller 114 is programmed to cause the pressurization device to provide a sufficient vacuum to keep substantially all of each region of the temperature-controlled surface between air-egress features in thermal contact with the subject's skin. This provides a relatively large contact interface for efficient heat transfer with the target tissue.

Different vacuum levels can be utilized during treatment sessions. For example, relatively strong vacuums can be used to pull the subject's tissue into the applicator. A weaker vacuum can be maintained to hold the subject's tissue against the thermally conductive surface. If suitable thermal contact is not maintained (e.g., the subject's skin moves away from the thermally conductive surface), the vacuum level can be increased to reestablish suitable thermal contact. In other procedures, a generally constant vacuum level can be used throughout the treatment session.

If the treatment system 100 includes multiple applicators, a treatment profile can include specific profiles for each applicator to concurrently or sequentially treat multiple treatment sites, including, but not limited to, sites along the subject's torso, abdomen, legs, buttock, legs, face and/or neck (e.g., submental sites, submandibular sites, etc.), knees, back, arms, ankle region, or other treatment sites. The vacuum levels can be selected based on the configuration of the cup. Strong vacuum levels can be used with relatively deep cups whereas weak vacuum levels can be used with relatively shallow cups. The vacuum level and cup configuration can be selected based on the treatment site and desired volume of tissue to be treated. In some embodiments, the controller 114 can be incorporated into the applicator 102 or another component of the treatment system 100.

D. Applicators

Figure 4:
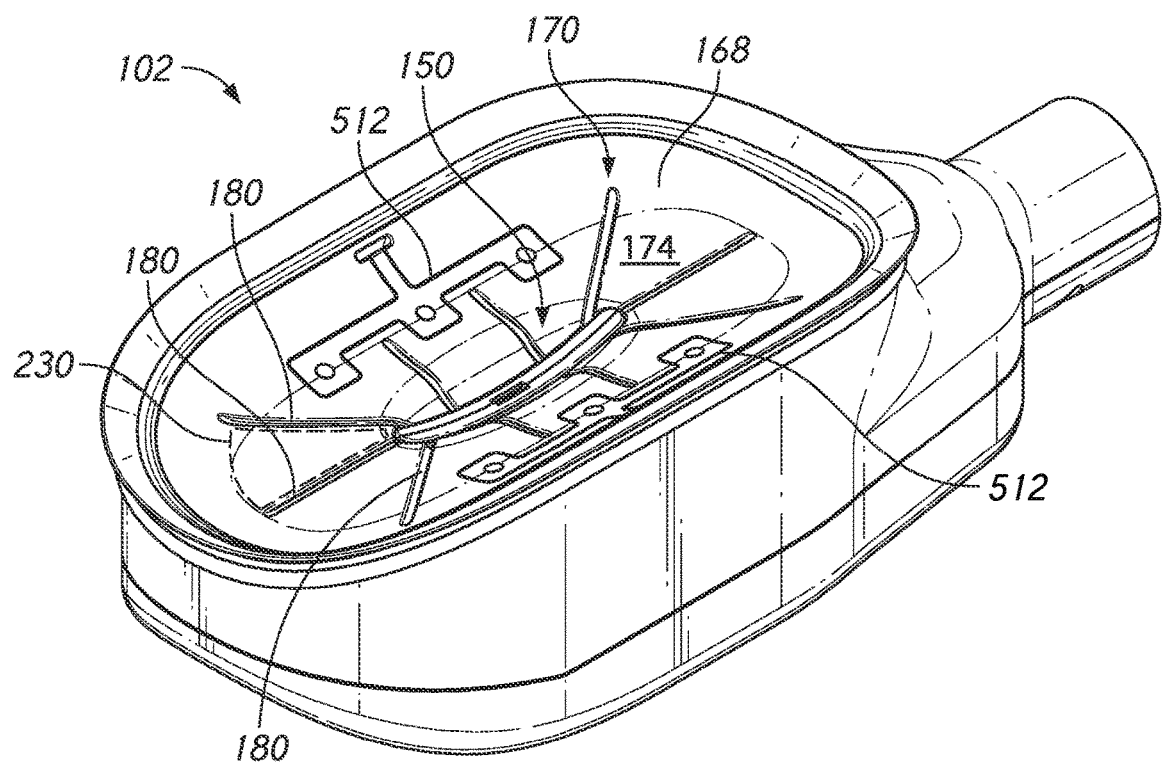
FIG. 4 is an isometric view of an applicator suitable for use with the system of FIG. 1 in accordance with an embodiment of the technology.
Figure 5:
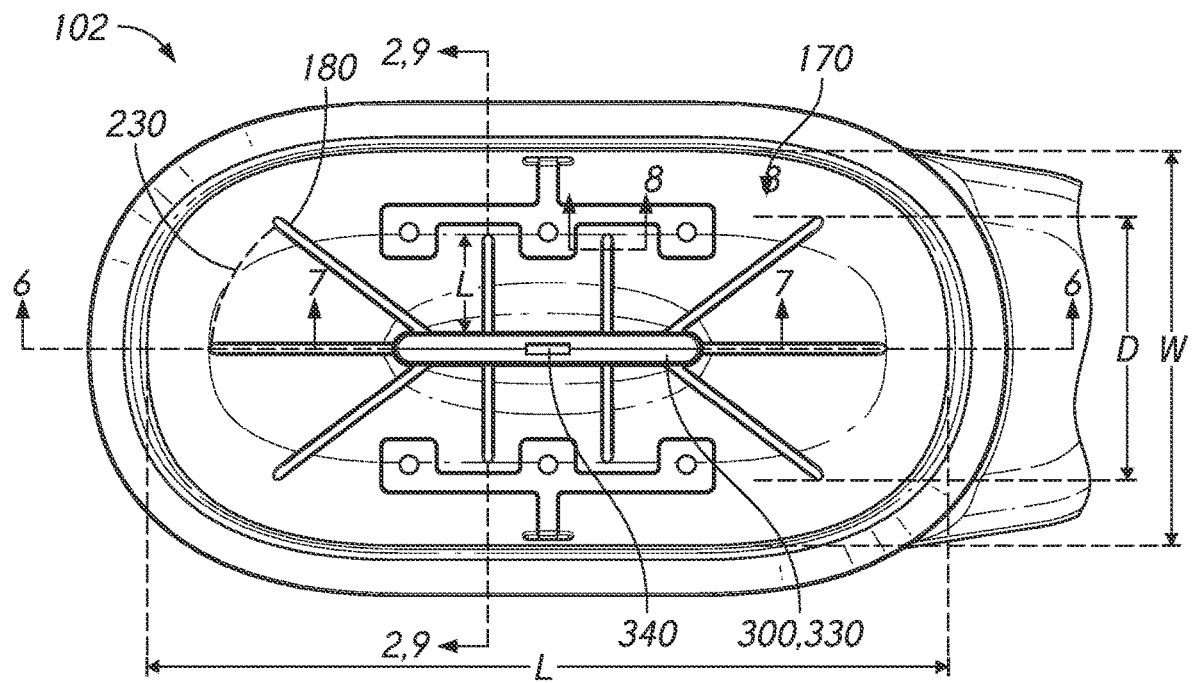
FIG. 5 is a bottom view of the applicator of FIG. 4.

FIG. 4 is an isometric view of an applicator 102, and FIG. 5 is a bottom plan view of the applicator 102. The cup 168 has a topography for removing air from the cavity 170 because it has air-egress features 180 extending outwardly from the central region 150 such that a significant portion of the temperature-controlled surface 174 is located directly between the air-egress features 180. The subject's skin (or liner) can be pulled against the areas (e.g., one area 230 is indicated in dashed line) of the temperature-controlled surface 174 located between adjacent air-egress features 180. In various embodiments, at least 50%, 60%, 70%, 80%, 90%, or 95% of total area of the exposed temperature-controlled surface 174 facing the tissue-receiving cavity 170 can be located between the air-egress features 180. In some embodiments, a ratio of a sum of areas of the temperature-controlled surface 174 located directly between the air-egress features 180 to a total area of the temperature-controlled surface 174 is equal to or greater than 0.5, 0.6, 0.7, 0.8, or 0.9. The ratio can be selected based on the tendency of air pockets to be present when the applicator 102 initially seals with the subject's skin. For example, a highly contoured temperature-controlled surface 174 can be prone to producing a large number of air pockets, so the ratio can be increased whereas the ratio can be reduced for a relatively shallow flat cup 168 with a gradually contoured temperature-controlled surface 174.

The air-egress features 180 can be spaced apart from one another or interconnected to define an airflow pattern suitable for evacuating air. Referring now to FIG. 5, air-egress features 180 can extend across most of a width W and/or length L of the tissue-receiving cavity 170. A distance D between outermost ends of opposing air-egress features 180 can be equal to or greater than about half the width W. The distance D can be measured in a direction generally perpendicular to the longitudinal length of the cavity 170. A ratio of the distance D to the width W can be equal to or greater than about 0.5, 0.6, 0.7, 0.8, or 0.9. In some embodiments, the temperature-controlled surface 174 can be gradually sloped to help avoid air pockets at its periphery, so the air-egress features 180 can be located at the central region 150 and may not extend across most of the width W and/or length L. Accordingly, the air-egress features 180 or portions thereof can be localized at locations susceptible to air pocket formation.

Figure 6:
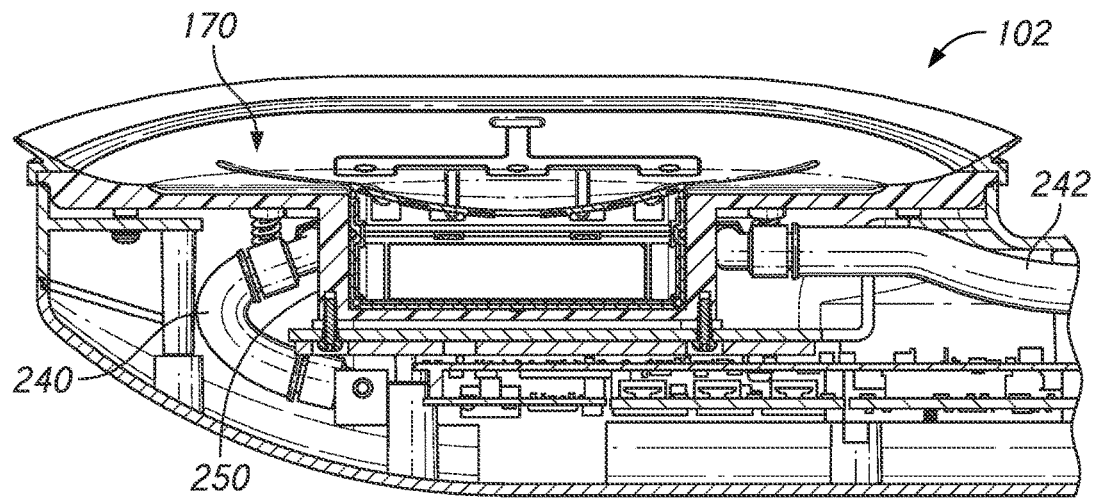
FIG. 6 is a cross-sectional view of an applicator taken along line 6-6 of FIG. 5 in accordance with an embodiment of the technology.
Figure 7:
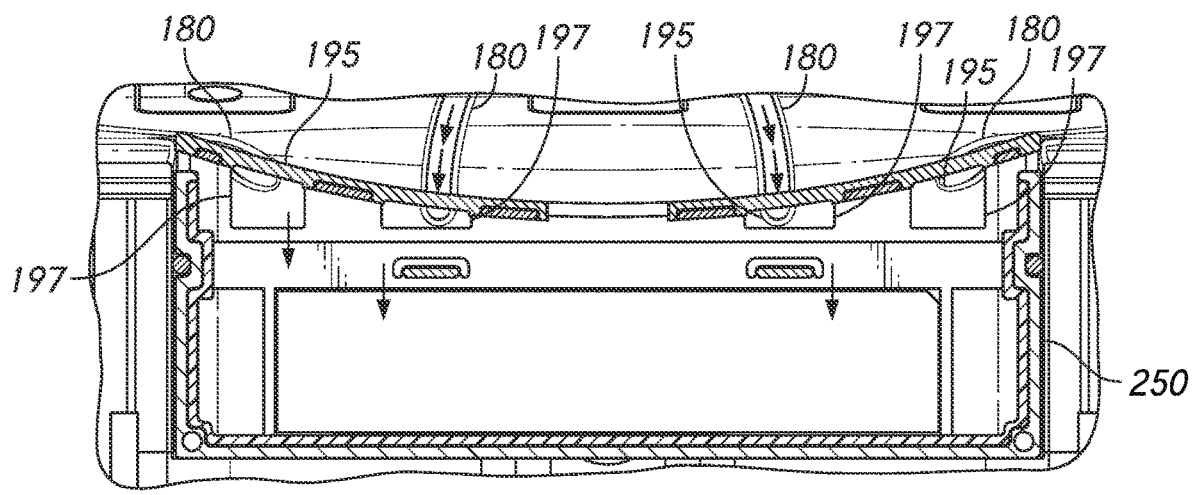
FIG. 7 is a cross-sectional view of an applicator taken along line 7-7 of FIG. 5 in accordance with an embodiment of the technology.

FIG. 6 is a cross-sectional view of the applicator 102 taken along line 6-6 of FIG. 5 in accordance with an embodiment of the technology. FIG. 7 is a cross-sectional view of the applicator 102 taken along line 7-7 of FIG. 5. Referring now to FIG. 6, lines 240, 242 can be in fluid communication with the cavity 170 via a manifold device 250. The manifold device 250 can include vacuum ports, channels, valves, regulators, sensors, or the like. An internal controller or circuitry assembly of the manifold device 250 can be in electrical communication with sensors, valves, or other components.

Referring now to FIG. 7, air-egress features 180 can be in fluid communication with corresponding vacuum ports 197. During use, air can flow along the air-egress features 180 (indicated by arrows) and through the vacuum ports 197, manifold device 250, and lines 240, 242 (FIG. 6). The lines 240, 242 can be in fluid communication with conduits (e.g., conduits 180*a*, 180*b* of FIG. 3) or other components of the connector 104. In other embodiments, air-egress features 180 can be connected to a single vacuum port, such as a slot, an opening, or other aperture. The number, positions, and configuration of the vacuum ports can be selected based on the desired flow rates, vacuum distribution, and/or characteristics of applied substances at the tissue/applicator interface.

Figure 8:
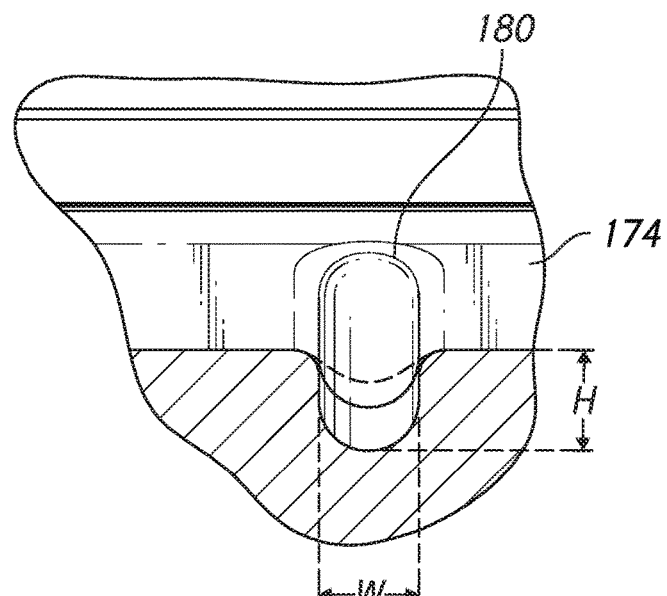
FIG. 8 is a cross-sectional view of the applicator taken along line 8-8 of FIG. 5 in accordance with an embodiment of the technology.

FIG. 8 is a cross-sectional view of the applicator 102 taken along line 8-8 of FIG. 5 in accordance with an embodiment of the technology. Dimensions of the air-egress features 180 can be selected to limit the area of the subject's tissue (or liner) not in direct contact with the surface 174. In some embodiments, the air-egress feature 180 has a height H of about 1 mm to about 2 mm, a width W of about 1 mm to about 2 mm, and a length L (FIG. 5) of at least 10 mm and can be generally U-shaped, V-shaped, or other suitable shape. In an another embodiment, the air-egress feature 180 is a U-shaped channel having a generally uniform cross-sectional profile along its longitudinal length. In other embodiments, the height H and/or width W can decrease in the direction away from the vacuum port 197. The dimensions, configuration, and characteristics of the air-egress feature 180 can be selected based on the desired airflow rates, position of the air-egress feature, or the like.

Figure 9:
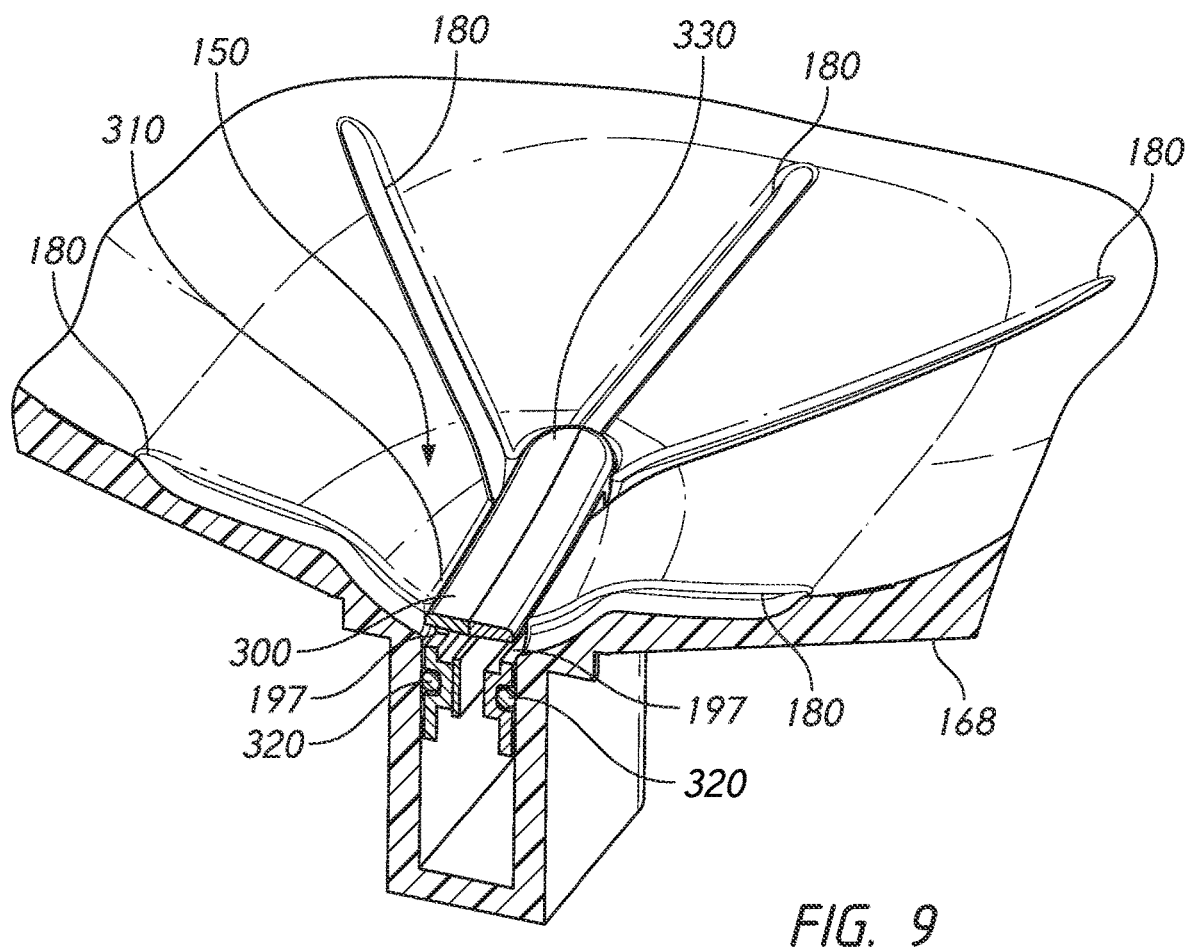
FIG. 9 is a isometric view of a central region of a cup taken along line 9-9 of FIG. 2 in accordance with an embodiment of the technology.

FIG. 9 is a isometric view of the central region 150 of the cup 168 taken along line 9-9 of FIG. 5 in accordance with an embodiment of the technology. A flow distributor 300 is positioned within an elongate central opening 310 of the cup 168. The flow distributor 300 can include an array of vacuum ports 197, sealing elements 320, valves, and other suitable elements for providing a desired vacuum. As shown in FIG. 5, the flow distributor 300 can include an air inlet 340 for drawing tissue against an upper region or plate 330 and can serve as a gel trap to prevent a cryoprotectant gel from flowing through the applicator 102.

With reference to FIG. 9, the cup 168 can be made of one or more thermally conductive materials, including, without limitation, metal (e.g., aluminum, stainless steel, pure copper, copper alloys, etc.) or other rigid or flexible high heat transfer materials, such as thermally conductive plastics. In some embodiments, the thermally conductive material of the cup 168 at room temperature has a thermal conductivity equal to or greater than about 25 W/(mK), 50 W/(mK), 100 W/(mK), 200 W/(mK), 300 W/(mK), 350 W/(mK), and ranges encompassing such thermal conductivities. The cup 168 can have a multi-piece construction with various pieces made of materials selected to provide different amounts of heat flow at different locations. In other embodiments, the cup 168 has a unitary construction and is made of a single material, such as metal. Additional vacuum ports can be positioned at suitable locations along the cup 168 based on, for example, considerations of patient comfort, desired vacuum levels, and/or other treatment parameters.

Figure 10:
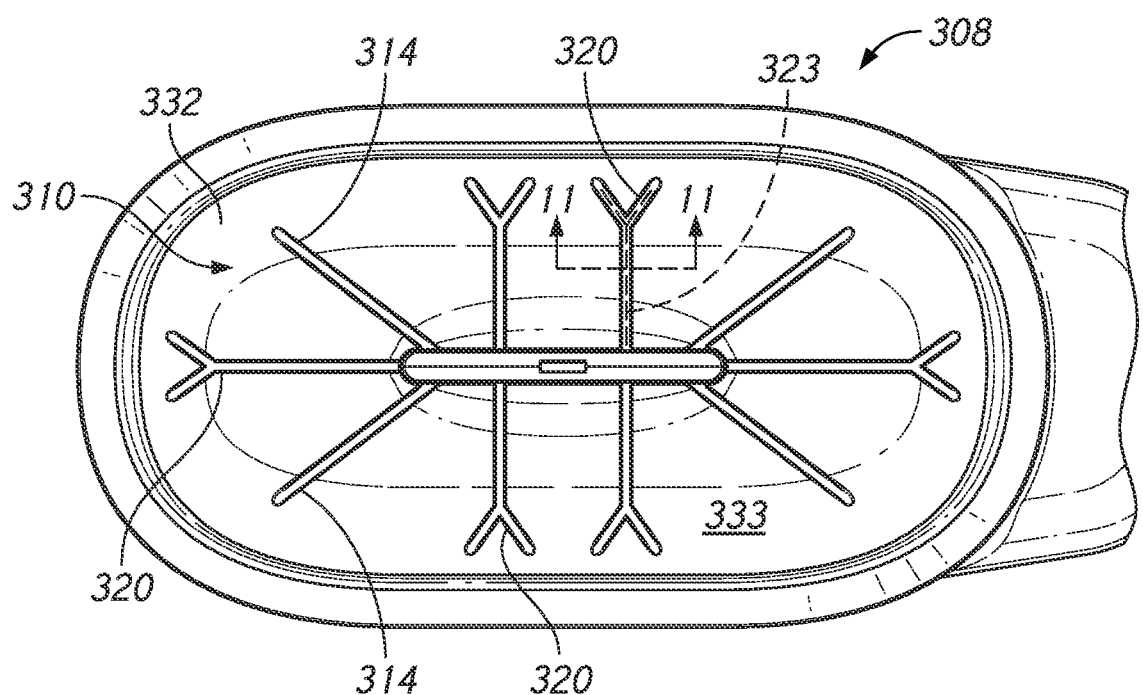
FIG. 10 is a bottom view of an applicator in accordance with another embodiment of the technology.
Figures 11, 12:
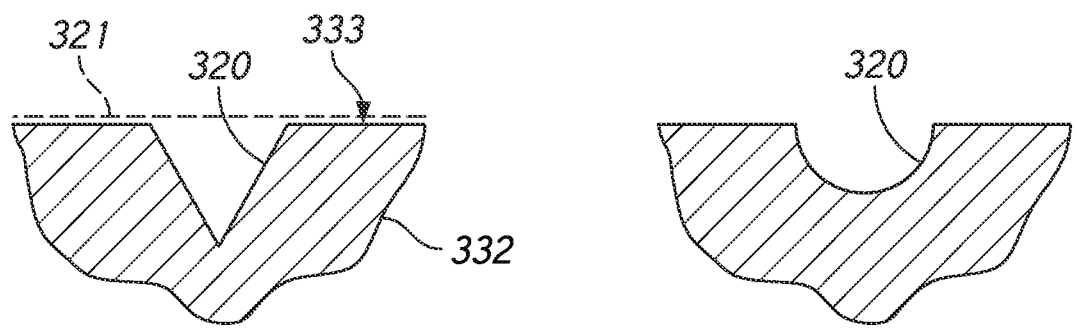
FIG. 11 is a cross-sectional view of an airflow feature taken along line 11-11 of FIG. 10.
FIGS. 12 and 13 are cross-sectional views of airflow feature in accordance with some embodiments of the technology.

FIG. 10 is a bottom view of an applicator 308 in accordance with an embodiment of the technology. The applicator 308 can include an airflow features 310 in the form of air-egress features 314 (two identified) and branching air-egress features 320 (two identified). The air-egress features 320, 314 can have geometrically congruent cross sections. In other embodiments, air-egress features 320, 314 can have geometries selected based on their location within the cavity. As shown in FIGS. 10 and 11, air-egress features 320 can be V-shaped channels extending along a cup 332. FIG. 11 shows the position 321 (illustrated in dashed line) of the skin surface extending across and covering the open end of the air-egress feature 320 such that air can flow along an air path (e.g., air path 323 is illustrated in dashed line in FIG. 10). Each air-egress feature 320 can maintain such an air path while the subject's tissue is held firmly against a surface 333 of the cup 332.

Figure 13:
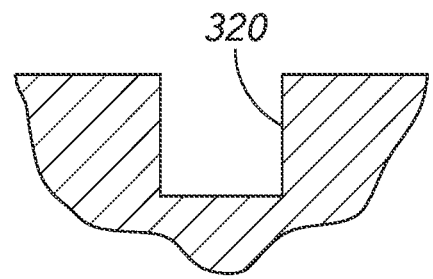

FIGS. 12 and 13 show cross-sectional profiles for the air-egress feature 320 in other embodiments. Referring now to FIG. 12, the air-egress feature 320 can have a semicircular cross-section and can be formed via machining or molding processes. Referring now to FIG. 13, air-egress feature 320 can have a polygonal or generally rectangular cross section formed via machining or molding processes.

Figure 14:
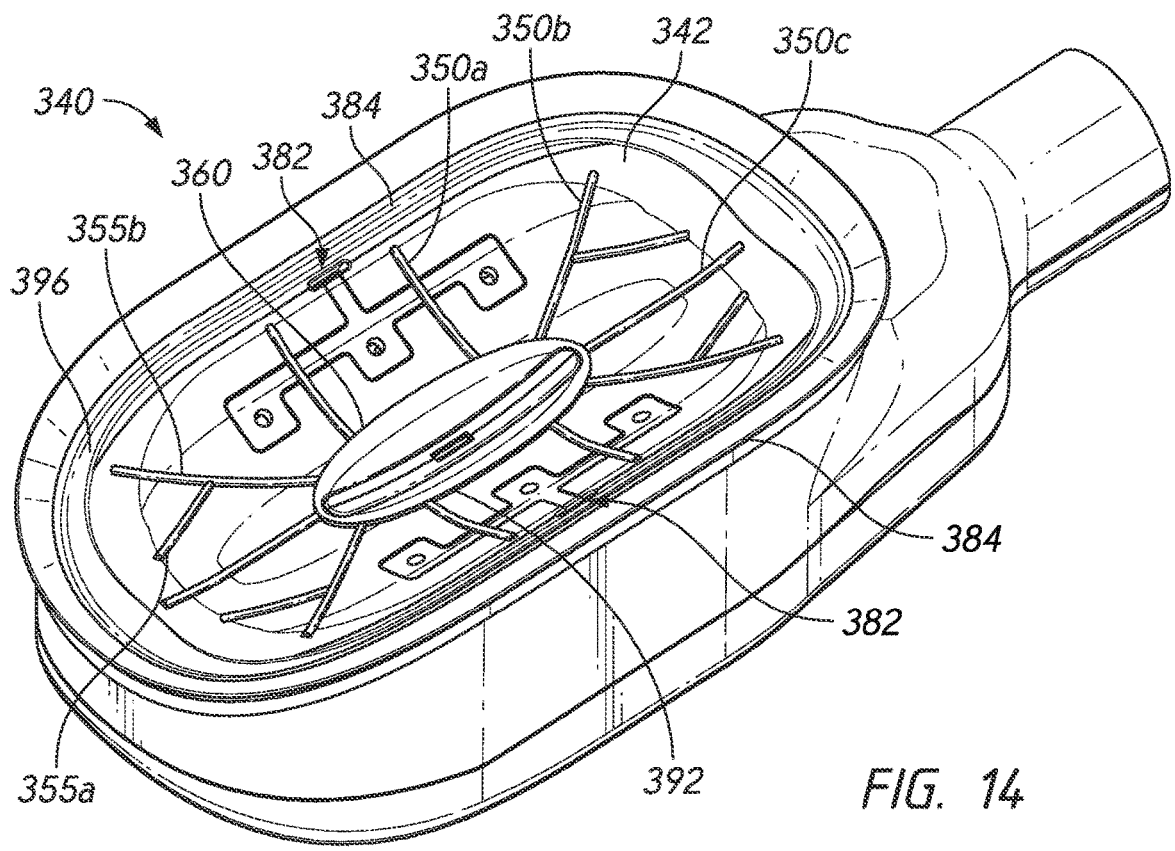
FIG. 14 is an isometric view of an applicator with branching airflow features in accordance with another embodiment of the technology.
Figure 15:
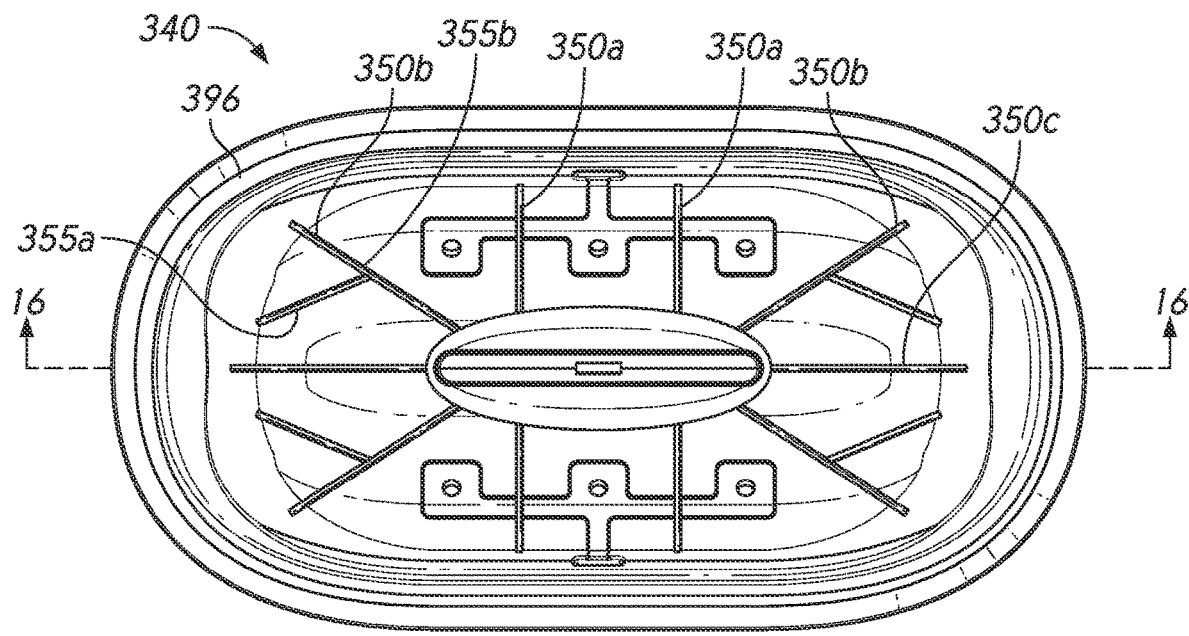
FIG. 15 is a bottom view of the applicator of FIG. 14.

FIG. 14 is an isometric view of an applicator 340 in accordance with another embodiment. FIG. 15 is a bottom view of the applicator 340. Relevant description of the applicators discussed in connection with FIGS. 1-13 applies to the applicator 340. Referring now to FIG. 14, applicator 340 can include a cup 342 and airflow features in the form of air-egress features 350*a*, 350*b*, 350*c* (collectively "air-egress features 350") that extend outwardly from a central region 360. Air-egress features 350*a* extend away from a central region 392 toward periphery portions 382 at longitudinal sides 384 of the cup 342. Air-egress features 350*b* extend toward corresponding rounded corners 396 of the cup 342 and branch to form terminal portions 355*a*, 355*b*. Air-egress features 350*c* can extend in a direction generally parallel to a longitudinal length of the cup 342.

Figure 16:
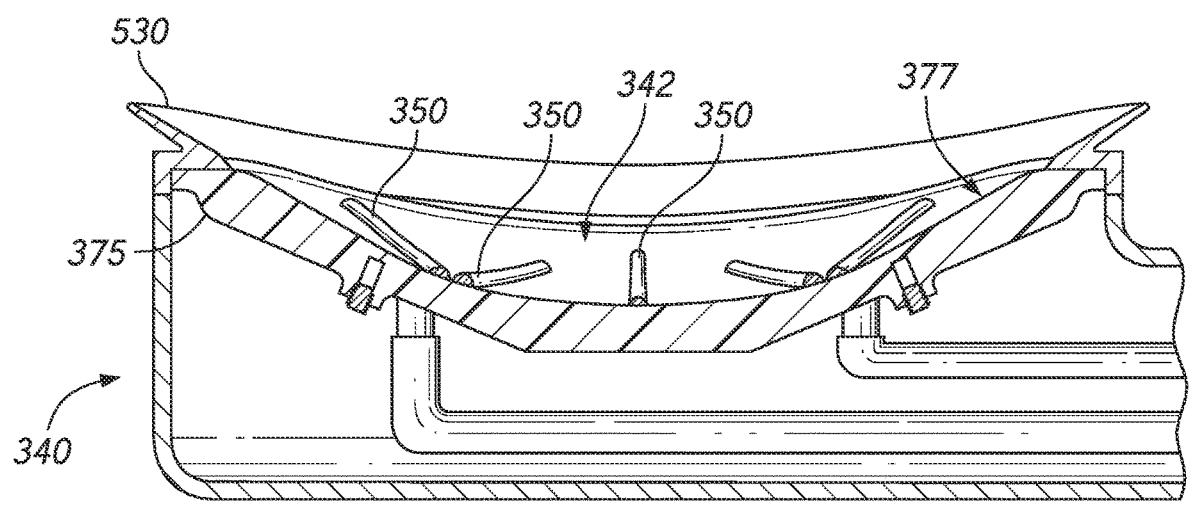
FIG. 16 is a cross-sectional view of an applicator taken along line 16-16 of FIG. 15 in accordance with an embodiment of the technology.

FIG. 16 is a cross-sectional view of the applicator 340 taken along line 16-16 of FIG. 15. Air-egress features 350 can be elongate protrusions coupled to or integrally formed with the cup 342. The cup 342 can include or be coupled to one or more thermal elements for controlling the temperature of a temperature-controlled surface 377.

Figure 17:
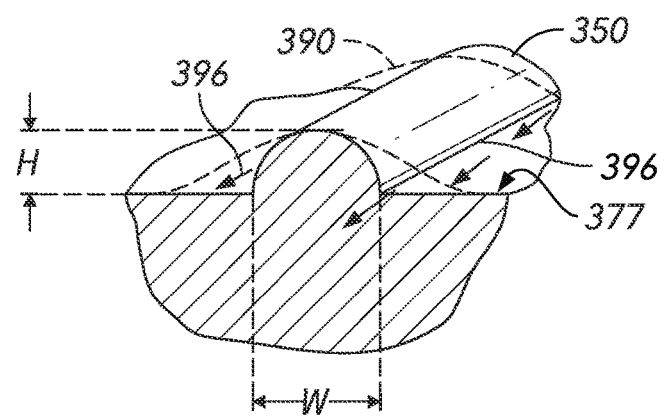
FIGS. 17 and 18 are cross-sectional views of airflow features located along a cup in accordance with embodiments of the technology.

FIG. 17 is a cross-sectional view of one of the air-egress features 350. The air-egress feature 350 has a rounded cross-sectional profile and can have a height H selected to maintain a gap between the surface 377 and the subject's skin 390 (illustrated in phantom line). When a vacuum is applied to draw the subject's skin 390 toward the surface 377, air flow paths 396 can be maintained along the longitudinal length of the air-egress feature 350. In the illustrated embodiment, air flow paths 396 are located on opposite sides of the air-egress feature 350. In some embodiments, the height H can be about 1 mm to about 2 mm, and a width W can be about 1 mm to about 2 mm. Other dimensions can be selected.

Figure 18:
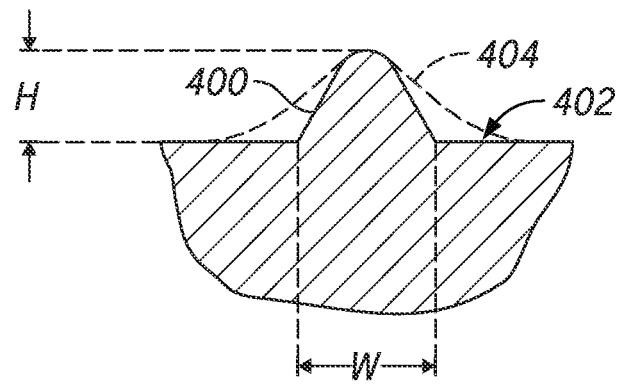

FIG. 18 is a cross-sectional view an air-egress feature 400 having a rounded triangular cross-sectional profile. The height H of the feature 400 can be selected to maintain a gap between a cup surface 402 and the subject's skin 404 (illustrated in phantom line). In some embodiments, the height H can be about 1 mm to about 3 mm, and a width W can be about 0.5 mm to about 2 mm. When a vacuum is applied to draw the subject's skin 404 toward the surface 402, air flow paths can be maintained along the longitudinal length of the air-egress feature 400. Although FIG. 16 shows the applicator with protrusion air-egress features, applicators can include both channel airflow features and protrusion airflow features.

E. Treatment Methods

Figure 19:
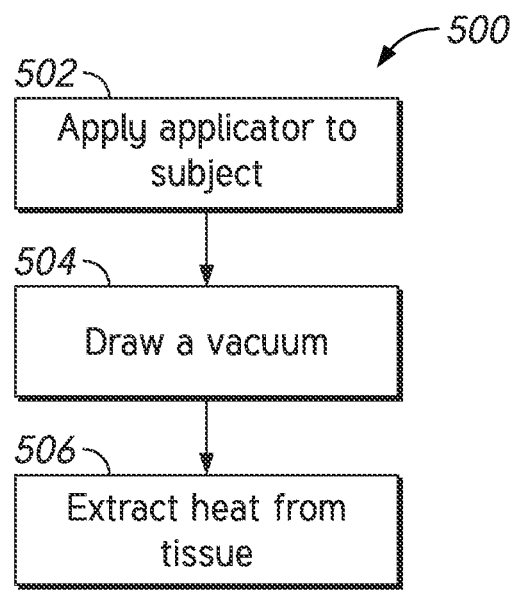
FIG. 19 is a flowchart of a method for treating a subject in accordance with embodiments of the disclosed technology.

FIG. 19 is a flowchart of a method 500 for treating a subject in accordance with embodiments of the disclosed technology. Generally, an applicator can be applied to the treatment site and a vacuum can be drawn to pull tissue into a tissue-receiving cavity of the applicator. The subject's skin can be drawn toward a conductive surface of a temperature-controlled cup while air-egress features maintain airflow paths for removing air from the cavity. After the skin is in thermal contact with the temperature-controlled cup, heat is extracted from the subject's tissue to cool the tissue an amount sufficient to be biologically effective in selectively damaging and/or reducing the subject's subcutaneous lipid-rich cells. Details of the method 500 are discussed in connection the embodiments shown in FIGS. 1-13.

At block 502, an applicator can be applied to the subject's skin. The applicator can be prepared for treatment by installing an appropriate contoured lip, liner, etc. for the treatment site. As discussed in connection with FIG. 2, the sealing element 151 can be placed against the subject to form a seal suitable for maintaining a desired vacuum within the tissue-receiving cavity 170.

With reference to FIG. 2, the sealing element 151 can include a contoured lip 530 and a body 532. The lip 530 can define an entrance and can be configured to sealingly engage, for example, the subject's skin. For example, the lip 530 can be configured for forming airtight seals with the subject's skin and can be made, in whole or in part, of silicon, rubber, soft plastic, or other suitable highly compliant materials. The mechanical properties, thermal properties, shape, and/or dimensions of the contoured lip 530 can be selected based on, for example, whether it contacts the subject's skin, liner assembly, a cryoprotectant gel pad, or the like. The body 532 is coupled to a housing 544. As tissue is pulled through the entrance of the sealing element 151 and toward the cup 168, the flared lip 530 can deflect outwardly.

Different sealing elements or cups can be installed on the base unit 152 for treatment flexibility. The geometries of the contoured sealing element 151 and cup 168, which can be replaced, can be selected to conform to a contour of a cutaneous layer. The sides, waistline, and other features of the contoured heads can be selected to facilitate conformation of heads to the contours of individual target areas. For example, the shape of a typical human torso may vary between having a relative large radius of curvature, e.g., on the stomach or back, and having a relatively small radius of curvature, e.g., on the abdominal sides. Moreover, the size of a cup having an approximately consistent curvature may vary. The sealing elements may be fitted to individual lipid-rich cell deposits to achieve an approximately air-tight seal, achieve the vacuum pressure for drawing tissue into an interior cavity for treatment, maintain suction to hold the tissue, massage tissue (e.g., by altering pressure levels), and use little or no force to maintain contact between an applicator and a patient.

Components can be attached and detached in a plurality of combinations to achieve a desired contour for a treatment. Accordingly, a single base unit and/or umbilical cable may be combined with a set of interchangeable heads and/or cups to form a wide variety of contours for treating different lipid-rich cell deposits in a cost effective manner. Further, a practitioner performing the treatment can demonstrate their expertise to the patient by tailoring the applicator contour to the specific body parts being treated. In this manner, the patient understands that their treatment is customized to their body for better comfort and for better treatment results.

Tissue-receiving cavities disclosed herein can have substantially U-shaped cross sections, V-shaped cross sections, or partially circular/elliptical cross-sections, as well as or other cross sections suitable for receiving tissue. Thus, thermal properties, shape, and/or configuration of the cup 168 can be selected based on, for example, target treatment temperatures and/or volume of the targeted tissue. Embodiments of the base units for treating large volumes of tissue (e.g., adipose tissue along the abdomen, hips, buttock, etc.) can have a maximum depth equal to or less than about 2 cm, 5 cm, 10 cm, 15 cm, 20 cm, or 30 cm, for example. Embodiments of the base units for treating small volumes (e.g., a small volume of submental tissue) can have a maximum depth equal to or less than about 0.5 cm, 2 cm, 2.5 cm, 3 cm, or 5 cm, for example. The maximum depth of the tissue-receiving cavity 170 can be selected based on, for example, the volume of targeted tissue, characteristics of the targeted tissue, and/or desired level of patient comfort.

At block 504, a vacuum can be drawn while the sealing element 151 can be held against the subject. To draw the vacuum, the pressurization device 123 (FIG. 1) can operate to remove air from the tissue-receiving cavity 170 (FIG. 3) to urge tissue into the applicator 102. The pressure level can be selected to partially or completely fill the tissue-receiving cavity 170 with tissue. If the vacuum level is too low, tissue will not be drawn adequately into the cavity 170. The vacuum level can be increased to reduce or eliminate gaps between the skin surface and the temperature-controlled surface 174. If the vacuum level is too high, undesirable discomfort to the patient and/or tissue damage could occur. The vacuum level can be selected to comfortably pull the tissue into contact with the desired area of the applicator, and the skin and underlying tissue can be pulled away from the subject's body which can assist in cooling underlying tissue by, e.g., lengthening the distance between targeted subcutaneous fat and the muscle tissue.

In some treatments, tissue can be drawn into the tissue-receiving cavity 170 such that substantially all of the skin surface within the cavity 170 overlies the temperature-controlled surface 174. For example, 90%, 95%, 95%, or more of the surface area of the skin located in the cavity 170 can overlie the temperature-controlled surface 174. The number and dimensions of the air-egress features 180 can be increased or decreased to achieve desired thermal contact for a particular vacuum level. After a sufficient amount of tissue fills most or all of the cavity 170, the pressure level can be controlled to comfortably hold the tissue.

At block 506, the applicator 102 can extract heat from the tissue. The cup 168 can be designed for rapid cooling and/or heating to, for example, reduce treatment times and/or produce generally flat temperature profiles over the heat-exchanging surface 174 or a portion thereof. Because the subject's body heat can be rapidly conducted to the cup 168, the cooled skin can be kept at a generally flat temperature profile (e.g., ±3° C. of a target temperature) even though regions of the skin, or underlying tissue, may experience different amounts of blood flow. Because non-lipid-rich cells usually can withstand colder temperatures better than lipid-rich cells, the subcutaneous lipid-rich cells can be injured selectively while maintaining the non-lipid-rich cells (e.g., non-lipid-rich cells in the dermis and epidermis). Accordingly, subcutaneous lipid-rich cells in a subcutaneous layer can be cooled an amount sufficient to be biologically effective in affecting (e.g., damaging and/or reducing) such lipid-rich cells without affecting non-target cells to the same or greater extent. During cooling/heating, the tissue can fill substantially the entire cavity 170. In various embodiments, the air-egress features 180 can maintain airflow paths extending to the peripheral portion of the cup 168 such that the tissue occupies at least 80%, 90%, 92.5%, or 95% of the volume of the cavity 170. Accordingly, the subject's tissue can substantially fill an entire volume of the cavity 170. In one application, the subject's tissue fills 90% or more of the volume of the cavity 170.

The temperature-controlled surface 174 can thermally contact an area of the subject's skin equal to or less than about 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, 500 $cm^2$, or other suitable area. For example, the temperature-controlled surface area can be, for example, equal to or less than 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, or another suitable area. The temperature-controlled conductive surface 174 can be cooled to a temperature equal to or less than a selected temperature (e.g., 5° C., 0° C., –2° C., –5° C., –7° C., –10° C., –15° C., –20° C., –25° C., etc.) to cool most of the skin surface of the retained tissue. In one embodiment, most of a heat-exchanging surface 161 can be cooled to a temperature equal to or less than about 0° C., –2° C., –5° C., –10° C., or –15° C.

In contrast to invasive procedures in which coolant is injected directly into targeted tissue, the smooth temperature-controlled surface 174 (FIG. 7) can conductively cool tissue to produce a desired temperature in target tissue without bruising, pain, or other problems caused by injections and perfusion of injected fluid. For example, perfusion of injected fluid can affect the thermal characteristics of the treatment site and result in undesired temperature profiles. As such, the non-invasive conductive cooling provided by the applicator 102 can be more accurate than invasive procedures that rely on injecting fluids. Targeted tissue can be cooled from about –20° C. to about 10° C., from about 0° C. to about 20° C., from about –15° C. to about 5° C., from about –5° C. to about 15° C., or from about –10° C. to about 0° C. In one embodiment, liner can be kept at a temperature less than about 0° C. to extract heat from subcutaneous lipid-rich cells such that those cells are selectively reduced or damaged.

Although the illustrated applicator 102 of FIG. 1 is positioned along the hips, applicators can also be positioned to treat tissue at the thighs, buttock, abdomen, submandibular region, neck region, or other target regions. Applicators can reduce localized adipose tissue along the abdomen, hips, submental region, or the like. In procedures for reducing a double chin, the applicator can be sized and then aligned with and placed generally at the submental region (i.e., the submental triangle). It will be appreciated that the applicators disclosed herein can be placed at other locations along the patient's body and the orientation of the applicator can be selected to facilitate a relatively close fit.

Other elements, materials, components (e.g., gel pads, absorbents, etc.) can be located between the skin and the applicators. U.S. Pub. No. 2007/0255362 and U.S. Patent Publication No. 2008/0077201 and U.S. application Ser. No. 14/610,807 disclose components, materials (e.g., coupling gels, cryoprotectants, compositions, etc.), and elements (e.g., coupling devices, liners/protective sleeves, absorbents, etc.) that can be placed between the skin and the applicator. The control module 106 (FIG. 1) can automatically perform various acts. For example, upon installation of the head, the control module 106 can automatically select a pressurization level suitable for drawing the liner into the base unit. Once the liner has been applied to the conductive cup, the control module 106 can notify a user to, for example, inspect the liner, apply the applicator, or perform another task. The control module 106 (FIG. 1) can then command the pressurization device 123 to draw tissue into the applicator 102. The control module 106 can notify the operator that the applicator 102 is ready for treatment based on sensor reading. The operator can inspect the applicator 102 and can begin treatment using the control module 106.

It will be appreciated that while a region of the body has been cooled or heated to the target temperature, in actuality that region of the body may be close but not equal to the target temperature, e.g., because of the body's natural heating and cooling variations. Thus, although the applicator 102 may attempt to heat or cool the target tissue to the target temperature or to provide a target heat flux, sensors 512 (FIG. 4) may measure a sufficiently close temperature or heat flux. If the target temperature or heat flux has not been reached, operation of the cooling unit can be adjusted to change the heat flux to maintain the target temperature or "set-point" selectively to affect targeted tissue. When the prescribed segment duration expires, the next treatment profile segment can be performed.

Sensors 512 can be temperature sensors, such as thermistors, positioned to detect temperature changes associated with warm tissue being drawn into and/or located in the cup 168. A control module (e.g., control module 106 of FIG. 1) can interpret the detected temperature increase associated with skin contact and can monitor, for example, the depth of tissue draw, tissue, freezing, thawing, or the like. In some embodiments, sensors 512 can be adjacent to the air-egress features 180 and can measure heat flux and/or pressure (e.g., contact pressure) with the skin of the patient. In yet further embodiments, the sensors 512 can be tissue impedance sensors, contact sensors, or other sensors used to determine the presence of tissue and/or whether tissue has been adequately drawn into the applicator so as to completely fill the cavity 170 to achieve a suitable level of thermal contact, limit or reduce voids or gaps, and/or hold tissue while limiting or reducing, for example, pooling of blood, discomfort, and so forth.

Sensor feedback can be collected in real-time and used in concert with treatment administration to efficaciously target specific tissue. The sensor measurements can also indicate other changes or anomalies that can occur during treatment administration. For example, an increase in temperature detected by the sensors 512 can indicate either a freezing event at the skin or movement of the applicator 102. An operator can inspect the subject's skin and/or applicator 102 in response to a detected increase in temperature. Methods and systems for collection of feedback data and monitoring of temperature measurements are described in commonly assigned U.S. Pat. No. 8,285,390.

The treatment procedures disclosed herein can also involve use of cryoprotectant between the applicator and skin. The cryoprotectant can be a freezing point temperature depressant that may additionally include a thickening agent, a pH buffer, a humectant, a surfactant, and/or other additives. The temperature depressant may include, for example, polypropylene glycol (PPG), polyethylene glycol (PEG), dimethyl sulfoxide (DMSO), or other suitable alcohol compounds. In a particular embodiment, a cryoprotectant may include about 30% polypropylene glycol, about 30% glycerin (a humectant), and about 40% ethanol. In another embodiment, a cryoprotectant may include about 40% propylene glycol, about 0.8% hydroxyethylcellulose (a thickening agent), and about 59.2% water. In a further embodiment, a cryoprotectant may include about 50% polypropylene glycol, about 40% glycerin, and about 10% ethanol. Other cryoprotectants or agents can also be used and can be carried by a cotton pad or other element. U.S. application Ser. No. 14/610,807 is incorporated by reference in its entirety and discloses various compositions that can be used as cryoprotectants.

It may take a few days to a few weeks, or longer, for the adipocytes to break down and be absorbed. A significant decrease in fat thickness may occur gradually over 1-3 months following treatment. Additional treatments can be performed until a desired result is achieved. For example, one or more treatments can be performed to substantially reduce (e.g., visibly reduce) or eliminate targeted tissue.

During a treatment session, contoured heads, line assemblies, and other components can be quickly replaced any number of times. Other types of heads, contours, and engagement features can be attached to the base unit 103. For example, contour elements disclosed in U.S. Publication 2010/0280582 can be used with the base unit 103, which may have magnets or other alignment features and can provide desired sealing, including generally air-tight seal cincturing. U.S. Publication 2010/0280582 is incorporated by reference in its entirety.

Liners can be used and can include films, sheets, sleeves, or other components suitable for defining an interface surface to prevent direct contact between surfaces of the applicator and the subject's skin to reduce the likelihood of cross-contamination between patients, minimize cleaning requirements, etc. Exemplary protective liners can be sheets, sleeves, or other components constructed from latex, rubber, nylon, Kevlar®, or other substantially impermeable or semi-permeable material. For example, the liner can be a latex sheet coated with a pressure-sensitive adhesive. Further details regarding a patient protection device may be found in U.S. Patent Publication No. 2008/0077201. In some procedures, a liner or protective sleeve may be positioned between an absorbent and the applicator to shield the applicator and to provide a sanitary barrier that is, in some embodiments, inexpensive and thus disposable. After installing the liner assembly, gel traps, filters, valves, and other components can be installed to keep applied substances (e.g., coupling gels, cryoprotectants, etc.) from being sucked into and/or through the base unit 103. In some embodiments, the liner 119 is configured to allow air to pass when drawing a vacuum and to restrict passage of a gel.

Embodiments according to the present disclosure may provide one or more additional advantages. For example, the size, shapes, and other physical properties of the base units, liner assemblies, sealing members, gaskets, contoured heads, and components of the applicators may be selected to accommodate heat removal sources (e.g., thermal devices, cooling devices, etc.) that may be used/reused with individual applicators. Modifications to flexible portions of individual applicators may enable the use of a standard heat removal source and accommodate different contours of individual cutaneous layers. In turn, this may make it possible to reuse base units, sealing members, liners, and/or contoured heads for different treatments. The rigid portions of the applicators (e.g., edge or mounting region of base unit), which are relatively stiff with respect to the flexible portions, provide an attachment point for heat removal sources that may resist bowing into the interior cavity and possibly separating from the heat removal sources when a vacuum (including a partial vacuum) is drawn into the applicators. Disposing temperature sensors inside the applicators, along temperature-controlled surfaces, within contoured heads, along liner assemblies, etc. may more accurately measure the temperature of skin surface, subcutaneous tissue, and so forth. The flexible portions of the applicator (e.g., flexible mouth) also allows some compliance to different subject body contours or geometries.

F. Computing Environments

Figure 20:
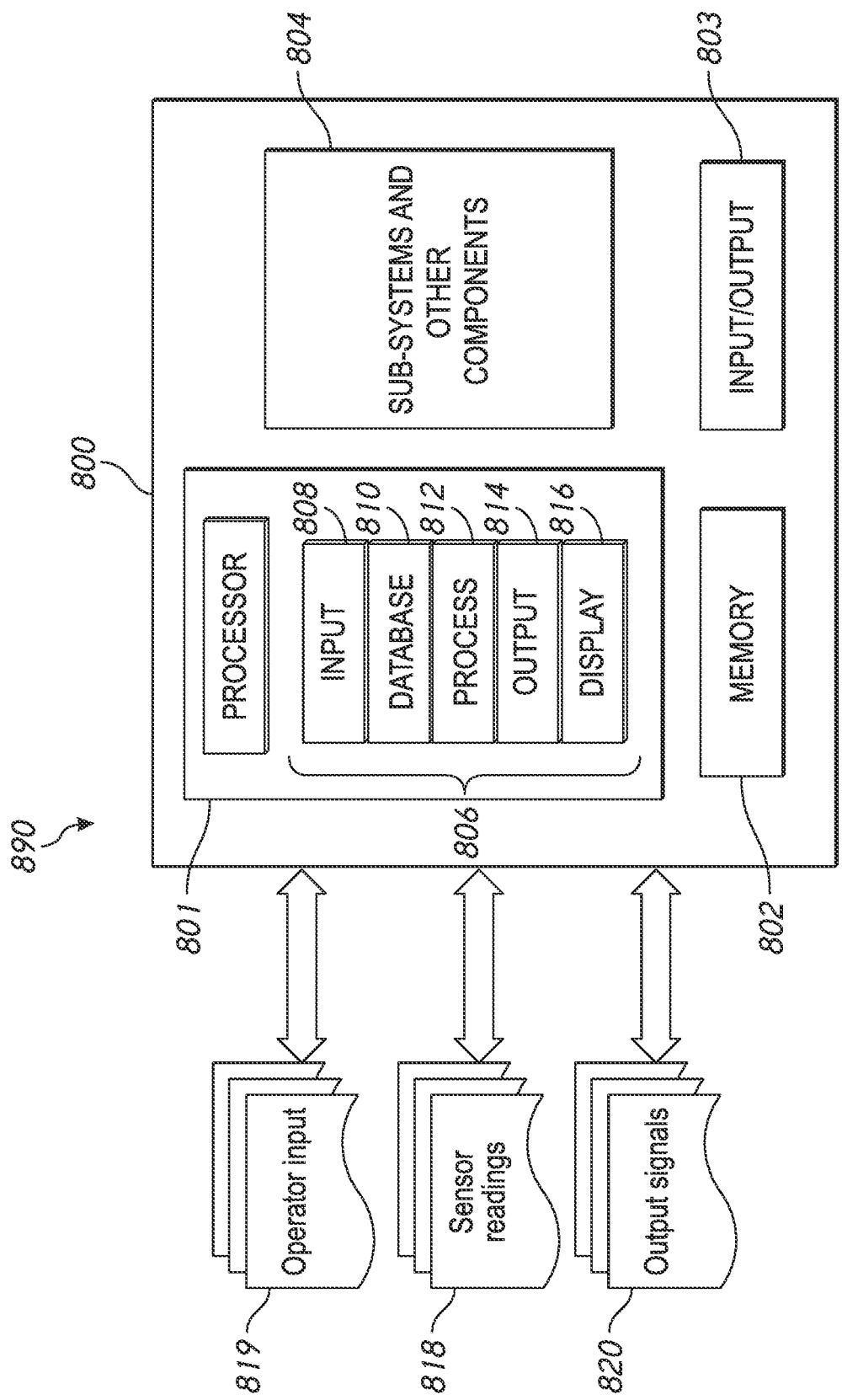
FIG. 20 is a schematic block diagram illustrating subcomponents of a controller in accordance with embodiments of the disclosed technology.

FIG. 20 is a schematic block diagram illustrating subcomponents of a controller in accordance with an embodiment of the disclosure. The controller can be part of the control module 106 (FIG. 1). For example, a controller 790 can be the controller 114 of FIG. 1 or can be incorporated into the applicators or other components disclosed herein. The controller 790 can include a computing device 800 having a processor 801, a memory 802, input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 20, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors and/or other data sources, and the output module 814 can communicate operator input to external computing devices and control variables to the controller. The display module 816 can be configured to convert and transmit processing parameters, sensor readings 818, output signals 820, input data, treatment profiles and prescribed operational parameters through one or more connected display devices, such as a display screen 118 (FIG. 1), printer, speaker system, etc.

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation. In various embodiments, the memory 802 can be flash memory, secure serial EEPROM, secure field programmable gate array, or secure application-specific integrated circuit. The memory 802 can store instructions for causing the applicators to cool/heat tissue, pressurization devices to draw a vacuum, or other acts disclosed herein. Vacuum levels can be selected based on characteristics of the applicator, airflow features, and/or treatment site. In one embodiment, the memory 802 stores instructions executable by the controller 790 for the thermal device to sufficiently cool conductive cups disclosed herein such that vacuum applicators non-invasively cool the subcutaneous lipid-rich cells to a desired temperature, such as a temperature less than about 0° C. In some embodiments, the memory 802 can contain liner installation or draw instructions for causing the liner to drawn into a, tissue draw instructions for causing the applicator to draw tissue into the applicator, treatment instructions for heating/cooling tissue, tissue release instructions for releasing tissue, and instructions for monitoring treatment. For example, the liner installation or draw instructions can be executed by the controller 790 to command the pressurization device 123 to suck the liner against a conductive surface of the conductive cup.

The input/output device 118 can include, without limitation, a touchscreen, a keyboard, a mouse, a stylus, a push button, a switch, a potentiometer, a scanner, an audio component such as a microphone, or any other device suitable for accepting user input and can also include one or more video monitor, a medium reader, an audio device such as a speaker, any combination thereof, and any other device or devices suitable for providing user feedback. For example, if an applicator moves an undesirable amount during a treatment session, the input/output device 803 can alert the subject and/or operator via an audible alarm. The input/output device 118 can be a touch screen that functions as both an input device and an output device. The control panel can include visual indicator devices or controls (e.g., indicator lights, numerical displays, etc.) and/or audio indicator devices or controls. The control panel may be a component separate from the input/output device 118 and/or output device 120, may be integrated applicators, may be partially integrated with one or more of the devices, may be in another location, and so on. In alternative embodiments, the controller 114 can be contained in, attached to, or integrated with the applicators. Further details with respect to components and/or operation of applicators, control modules (e.g., treatment units), and other components may be found in commonly-assigned U.S. Patent Publication No. 2008/0287839.

The controller 790 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

G. Conclusion

The treatment systems, applicators, and methods of treatment can be used reduce adipose tissue or treat subcutaneous tissue, acne, hyperhidrosis, wrinkles, structures (e.g., structures in the epidermis, dermis, subcutaneous fat, muscle, nerve tissue, etc.), and so on. Systems, components, and techniques for reducing subcutaneous adipose tissue are disclosed in U.S. Pat. No. 7,367,341 titled "METHODS AND DEVICES FOR SELECTIVE DISRUPTION OF FATTY TISSUE BY CONTROLLED COOLING" to Anderson et al., U.S. Patent Publication No. US 2005/0251120 titled "METHODS AND DEVICES FOR DETECTION AND CONTROL OF SELECTIVE DISRUPTION OF FATTY TISSUE BY CONTROLLED COOLING" to Anderson et al., and U.S. Patent Publication No. 2007/0255362 titled "CRYOPROTECTANT FOR USE WITH A TREATMENT DEVICE FOR IMPROVED COOLING OF SUBCUTANEOUS LIPID-RICH CELLS," the disclosures of which are incorporated herein by reference in their entireties. Vacuum applicators can stretch, stress, and/or mechanically alter skin to increase damage and fibrosis in the skin, affect glands, control freeze events (including initiating freeze events), etc. Methods for cooling tissue and related devices and systems in accordance with embodiments of the present invention can at least partially address one or more problems associated with conventional technologies as discussed above and/or other problems whether or not such problems are stated herein.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. An apparatus for treating a human subject, comprising:
    an applicator configured to cool a subject's skin and including
        a cup defining a tissue-receiving cavity and including a temperature-controlled surface,
        at least one vacuum port, and
        air-egress features extending along the temperature-controlled surface, the air-egress features are spaced circumferentially about and extend radially from the at least one vacuum port to provide airflow paths to the at least one vacuum port for removing air between the subject's skin and the cup while the at least one vacuum port provides a vacuum to draw tissue of the subject into thermal contact with the temperature-controlled surface located on opposite sides of each of the air-egress features, and wherein the air-egress features include channels and/or ridges.

2. The apparatus of claim 1, wherein the cup and vacuum port are configured such that when a vacuum is applied the subject's tissue substantially fills an entire volume of the tissue-receiving cavity except for small gaps created by the air-egress features formed on a surface of the cup.

3. The apparatus of claim 1, further comprising:
    a pressurization device in fluid communication with the tissue-receiving cavity via the at least one vacuum port; and
    a controller programmed to cause the pressurization device to operate to hold the subject's skin in thermal contact with the temperature-controlled surface while the cup conductively cools the tissue.

4. The apparatus of claim 3, wherein regions of the temperature-controlled surface are located between adjacent air-egress features, and wherein the controller is programmed to cause the pressurization device to provide a sufficient vacuum to keep substantially all of each region in thermal contact with the subject's skin.

5. The apparatus of claim 1, further comprising a pressurization device configured to draw a sufficient vacuum to eliminate air gaps between the subject's tissue and the temperature-controlled surface such that substantially no air gaps impair non-invasively cooling of the subject's subcutaneous lipid-rich cells to a temperature lower than about 0° C.

6. The apparatus of claim 1, wherein the air-egress features are configured to maintain airflow paths to the at least one vacuum port when the subject's tissue is operably received within the tissue-receiving cavity and a 12 inches Hg vacuum is drawn.

7. The apparatus of claim 1, wherein the cup is configured to non-invasively cool the subject's tissue, which is held in the tissue-receiving cavity, an amount sufficient to be biologically effective in damaging and/or reducing subcutaneous lipid-rich cells in the subject's tissue.

8. The apparatus of claim 1, wherein most of the temperature-controlled surface is located directly between the air-egress features.

9. The apparatus of claim 1, wherein a ratio of a sum of areas of regions of the temperature-controlled surface located directly between air-egress features to a total area of the temperature-controlled surface is greater than 0.5.

10. The apparatus of claim 1, wherein the air-egress features extend across most of a width and extend across most of a length of the tissue-receiving cavity.

11. The apparatus of claim 1, wherein the air-egress features are a network of elongate ridges and/or channels.

12. The apparatus of claim 1, wherein each of the air-egress features includes a first end spaced apart from a mouth of the cup, a second end positioned proximate the at least one vacuum port, and a main portion extending between the first and second ends and being dimensioned to allow thermal contact to be maintained between the subject's skin and an area of the temperature-controlled surface surrounding the first end and the main portion.

13. The apparatus of claim 1, wherein the air-egress features spread outwardly from a central region of the cup.

14. The apparatus of claim 1, wherein each of the air-egress features has a height of about 1 mm to 2 mm, a width about 1 mm to 2 mm, and a length of at least 10 mm.

15. The apparatus of claim 1, wherein the at least one vacuum port includes a plurality of vacuum ports each located at an end of a respective one of the air-egress features.

16. The apparatus of claim 1, wherein the applicator includes
    an elongate central region including the at least one vacuum port; and
    wherein the air-egress features include
        a first air-egress feature extending from a first side of the elongate central region,
        a second air-egress feature extending from a second side of the elongate central region, and a branching air-egress feature extending from an end of the elongate central region, the branching air-egress feature has
 a branching section with at least two terminal branches located along an upwardly slopped region of the cup, and
 an air-egress segment connecting the branching section to the elongate central region.

17. The apparatus of claim 1, wherein the air-egress features are U-shaped channels.

18. An apparatus for treating a human subject, comprising:
an applicator configured to cool tissue of the subject and including
 a cup having an interior surface at least partially defining a tissue-receiving cavity, wherein at least a portion of the interior surface is temperature-controlled, and
 a vacuum port extending through a central portion of the interior surface,
 wherein a topography of the interior surface is configured to form airflow paths along air-egress features extending along a surface of the cup, wherein the air-egress features extend longitudinally away from the central portion toward a peripheral portion of the interior surface when subcutaneous tissue of the subject is operably received within the cavity, wherein the air-egress features are spaced circumferentially about the central portion, wherein the cup and vacuum port are configured such that when a vacuum is applied the subject's tissue substantially fills an entire volume of the cup except for small gaps created by the air-egress features.

19. The apparatus of claim 18, wherein the air-egress features extend between the vacuum port and the peripheral portion and having heights sufficient to maintain the airflow paths when skin of the subject is drawn against most of the interior surface.

20. A method for treating a human subject, comprising:
applying an applicator to skin of the subject;
drawing a vacuum in a tissue-receiving cavity of the applicator to draw tissue of the subject toward a conductive surface of a temperature-controlled cup of the applicator to substantially fill an entire volume of the cup while air-egress features facing the tissue-receiving cavity maintain egress airflow paths for removing air located between the subject's skin and the temperature-controlled cup such that the skin of the subject thermally contacts regions of the temperature-controlled cup on opposite sides of at least one of the air-egress features, wherein the air-egress features are spaced circumferentially about and extend away from at least one vacuum port toward a periphery of the cup, wherein the at least one vacuum port is located at a bottom of the cavity; and
extracting heat from subcutaneous tissue of the subject via the conductive surface to cool the tissue an amount sufficient to be biologically effective in selectively damaging and/or reducing the subject's subcutaneous lipid-rich cells held in the tissue-receiving cavity.

21. The method of claim 20, further comprising maintaining a sufficient vacuum to hold the skin of the subject in thermal contact with substantially all of the conductive surface facing the tissue-receiving cavity while extracting heat from the subject's tissue.

22. The method of claim 20, further comprising drawing the tissue of the subject into the tissue-receiving cavity such that substantially all of the subject's skin located within the tissue-receiving cavity is in thermal contact with the conductive surface.

23. The method of claim 20, wherein the air-egress features extend across most of a width and a length of the tissue-receiving cavity.

* * * * *